United States Patent
Kaduchak et al.

(10) Patent No.: US 10,473,578 B2
(45) Date of Patent: Nov. 12, 2019

(54) SYSTEMS, METHODS, AND APPARATUSES FOR OPTICAL SYSTEMS IN FLOW CYTOMETERS

(71) Applicant: LIFE TECHNOLOGIES CORPORATION, Carlsbad, CA (US)

(72) Inventors: Gregory Kaduchak, Chandler, AZ (US); Wesley Smith, Junction Ciy, OR (US); Michael Ward, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 15/990,350

(22) Filed: May 25, 2018

(65) Prior Publication Data
US 2019/0033199 A1 Jan. 31, 2019

Related U.S. Application Data

(63) Continuation of application No. 15/633,613, filed on Jun. 26, 2017, now Pat. No. 10,018,553, which is a (Continued)

(51) Int. Cl.
*G01N 15/04* (2006.01)
*G01N 15/14* (2006.01)

(52) U.S. Cl.
CPC ..... *G01N 15/1459* (2013.01); *G01N 15/1404* (2013.01); *G01N 15/1434* (2013.01); *G01N 15/1456* (2013.01); *G01N 2015/1438* (2013.01)

(58) Field of Classification Search
CPC ....... G01N 15/1459; G01N 2015/1006; G01N 15/1434; G01N 15/1404; G01N 15/1436;
(Continued)

(56) References Cited

U.S. PATENT DOCUMENTS 5,999,250 A 12/1999 Hairston et al.
7,411,734 B2 8/2008 Magarill et al.
(Continued)

FOREIGN PATENT DOCUMENTS

CN 102175587 A 9/2011
EP 1884762 2/2008
(Continued)

OTHER PUBLICATIONS

Olson, R.J. et al., "An automated submersible flow cytometer for analyzing pico- and nanophytoplankton: FlowCytobot", *Deep Sea Research, Part 1; Oceanographic Research Papers*, Pergamon Press, Oxford, GB; vol. 50, No. 2, XP004558215, DOI: 10.1016/S0967-0637(03)00003-7, Feb. 1, 2003, 301-315.
(Continued)

*Primary Examiner* — Michael P Stafira
(74) *Attorney, Agent, or Firm* — BakerHostetler

(57) ABSTRACT

The present set of embodiments relate to a system, method, and apparatus for an optical configuration in a flow cytometer that allows for independent adjustment of focusing for each light source. Such systems, methods, and apparatuses require a final focusing element to be moved near the beginning of the optical train and for each optical element coming after the final focusing element to be configured to accommodate converging light beams while minimizing the introduction of aberrations into those beams.

19 Claims, 23 Drawing Sheets

Related U.S. Application Data continuation of application No. 14/607,677, filed on Jan. 28, 2015, now Pat. No. 9,726,593.

(60) Provisional application No. 62/041,806, filed on Aug. 26, 2014, provisional application No. 61/946,579, filed on Feb. 28, 2014.

(58) Field of Classification Search
CPC ......... G01N 2015/149; G01N 21/6428; G01N 15/147; G01N 15/14; G01N 2015/0065; G01N 15/1484; G01N 21/645; G01N 2015/1415; G01N 2015/1452; G01N 15/1429; G01N 2015/144; G01N 21/64; G01N 2021/6439; G01N 2015/1481; G01N 2015/1486; G01N 2021/6441; G01N 33/50; G01N 2015/1406; G01N 2015/1495; G01N 33/5091; G01N 15/1463; G01N 2015/008; G01N 2015/1438; G01N 2021/6421; G01N 2021/6482; G01N 21/6452; G01N 21/6456; G01N 15/1475; G01N 2021/6419; G01N 21/274; G01N 21/65; G01N 15/1456; G01N 2015/0073; G01N 2015/1075; G01N 2015/1447; G01N 2015/1497; G01N 2021/653; G01N 2035/00356; G01N 2035/0415; G01N 21/53; G01N 21/55; G01N 21/6458; G01N 2201/06113; G01N 2201/068; G01N 33/558; G01N 33/582; G01N 35/026; G01N 15/0211; G01N 15/1425; G01N 2015/0092; G01N 2015/1472; G01N 2035/00158; G01N 2035/00752; G01N 21/05; G01N 21/253; G01N 21/278; G01N 21/6486; G01N 21/6489; G01N 2201/12; G01N 33/5094; G01N 33/542; G01N 33/54313; G01N 33/54373; G01N 33/583; G01N 35/085; G01N 15/0227; G01N 15/10; G01N 15/1468; G01N 2015/0069; G01N 2015/0084; G01N 2015/0238; G01N 2015/145; G01N 2015/1454; G01N 2035/00742; G01N 21/25; G01N 21/272; G01N 21/4788; G01N 21/532; G01N 2201/04; G01N 2201/0691; G01N 27/4479; G01N 33/569; G01N 15/0272; G01N 15/1012; G01N 1/30; G01N 1/31; G01N 2015/0003; G01N 2015/0011; G01N 2015/0088; G01N 2015/025; G01N 2015/03; G01N 2015/0693; G01N 2015/1018; G01N 2015/1037; G01N 2015/1081; G01N 2015/1402; G01N 2015/142; G01N 2015/1422; G01N 2015/1445; G01N 2015/1477; G01N 2015/1479; G01N 2015/1493; G01N 2021/0346; G01N 2021/655; G01N 2035/00891; G01N 21/31; G01N 21/47; G01N 21/49; G01N 21/552; G01N 21/6402; G01N 21/6408; G01N 21/6445; G01N 21/8483; G01N 21/85; G01N 2201/0621; G01N 2201/0623; G01N 2201/10; G01N 2201/129; G01N 33/48; G01N 33/5035; G01N 33/53; G01N 33/57407; G01N 33/6875; G02B 21/04; G02B 21/361; G02B 27/0025; G02B 6/26; G02B 6/29365; G02B 21/0032; G02B 21/0076; G02B 21/0084; G02B 27/1006; G02B 27/141; G02B 27/142; G02B 5/04; G02B 5/285; G01B 11/272; G01J 3/36; G01J 3/4406; G01J 2003/104; G01J 3/0208; G01J 3/0218; G01J 3/14; G01J 3/433; G01J 3/44; G01J 3/4412; G01J 3/443

See application file for complete search history.

(56) References Cited

U.S. PATENT DOCUMENTS

| | | | |
|---|---|---|---|
| 8,376,551 | B2 | 2/2013 | Cobb |
| 9,726,593 | B2 | 8/2017 | Kaduchak et al. |
| 10,018,553 | B2 | 7/2018 | Kaduchak et al. |
| 2002/0093641 | A1 | 7/2002 | Ortyn et al. |
| 2002/0093902 | A1* | 7/2002 | Hirai ............... G11B 7/123 369/112.17 |
| 2003/0071996 | A1 | 4/2003 | Wang et al. |
| 2003/0156330 | A1* | 8/2003 | Edlinger ............ G02B 27/1026 359/618 |
| 2006/0066837 | A1 | 3/2006 | Ortyn et al. |
| 2006/0238757 | A1 | 10/2006 | Silcott |
| 2009/0122311 | A1 | 5/2009 | Kanda |
| 2009/0294702 | A1* | 12/2009 | Imanishi ............. G01N 21/274 250/576 |
| 2010/0157252 | A1 | 6/2010 | Itoh |
| 2011/0058163 | A1 | 3/2011 | Rich |
| 2014/0097129 | A1* | 4/2014 | Foster .............. B01L 3/502761 209/579 |
| 2014/0264097 | A1 | 9/2014 | Heanue et al. |
| 2015/0109585 | A1* | 4/2015 | Masuda ........... G03B 21/2033 353/31 |
| 2015/0168817 | A1* | 6/2015 | Cobb .................... G03B 21/14 353/31 |
| 2015/0211685 | A1* | 7/2015 | Foster .................... F17D 3/01 137/1 |
| 2017/0122869 | A1* | 5/2017 | Yoshikawa ....... G01N 15/1468 |
| 2017/0242266 | A1 | 8/2017 | Otani |

FOREIGN PATENT DOCUMENTS

| | | |
|---|---|---|
| JP | 05-061129 | 3/1993 |
| JP | H0643090 A | 2/1994 |
| JP | 09-508703 | 9/1997 |
| JP | 10228665 A | 8/1998 |
| JP | 2008-39539 | 2/2008 |
| WO | WO-1996/004543 | 2/1996 |
| WO | WO-2012/079103 | 6/2012 |

OTHER PUBLICATIONS

PCT/US2015/013279, , "International Preliminary Report on Patentability", dated Sep. 15, 2016, 11 pp.
PCT/US2015/013279, , "International Search Report and Written Opinion", dated Apr. 14, 2015, 15 pgs.

* cited by examiner

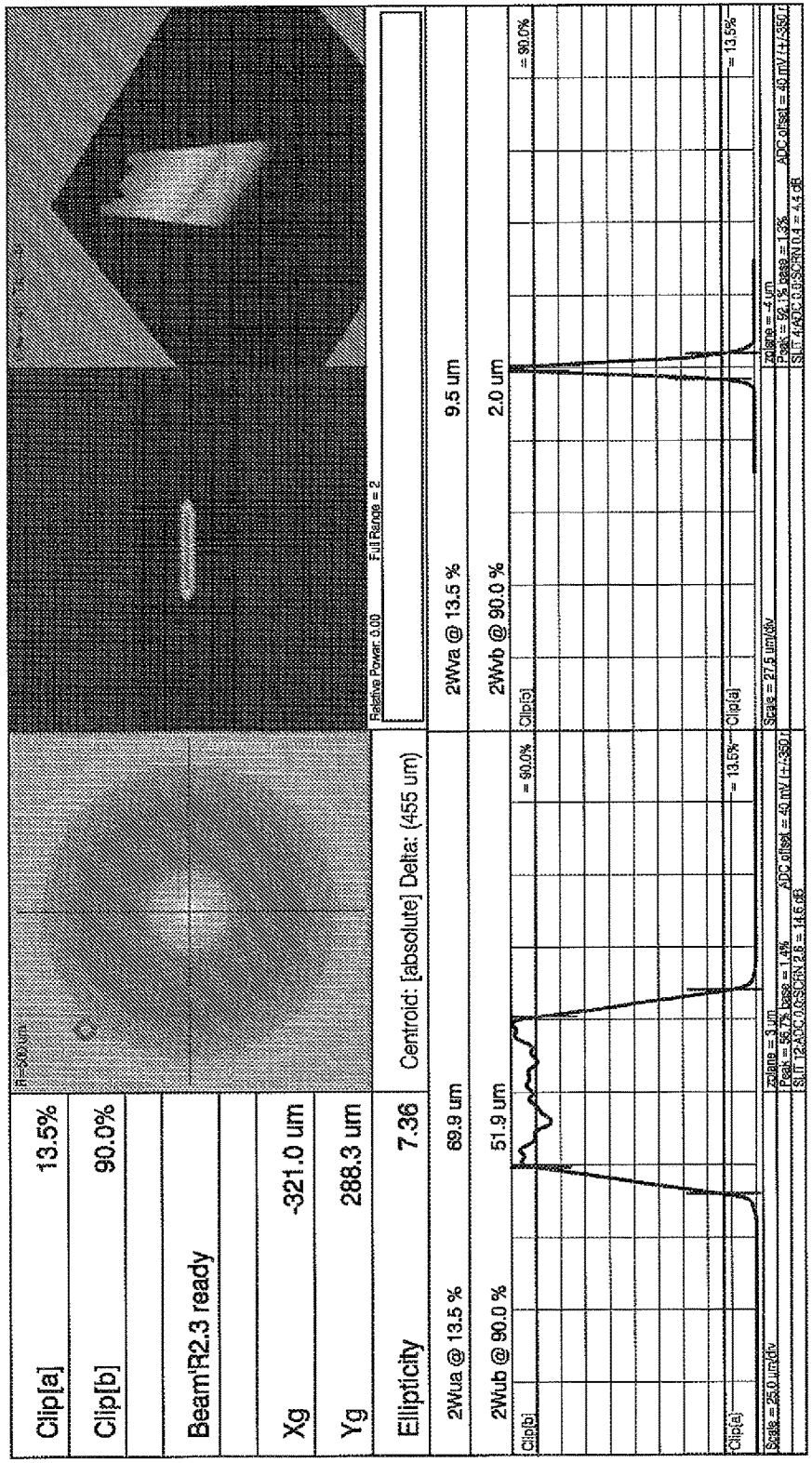
FIG. 8A  Blue Laser Beam at Focus

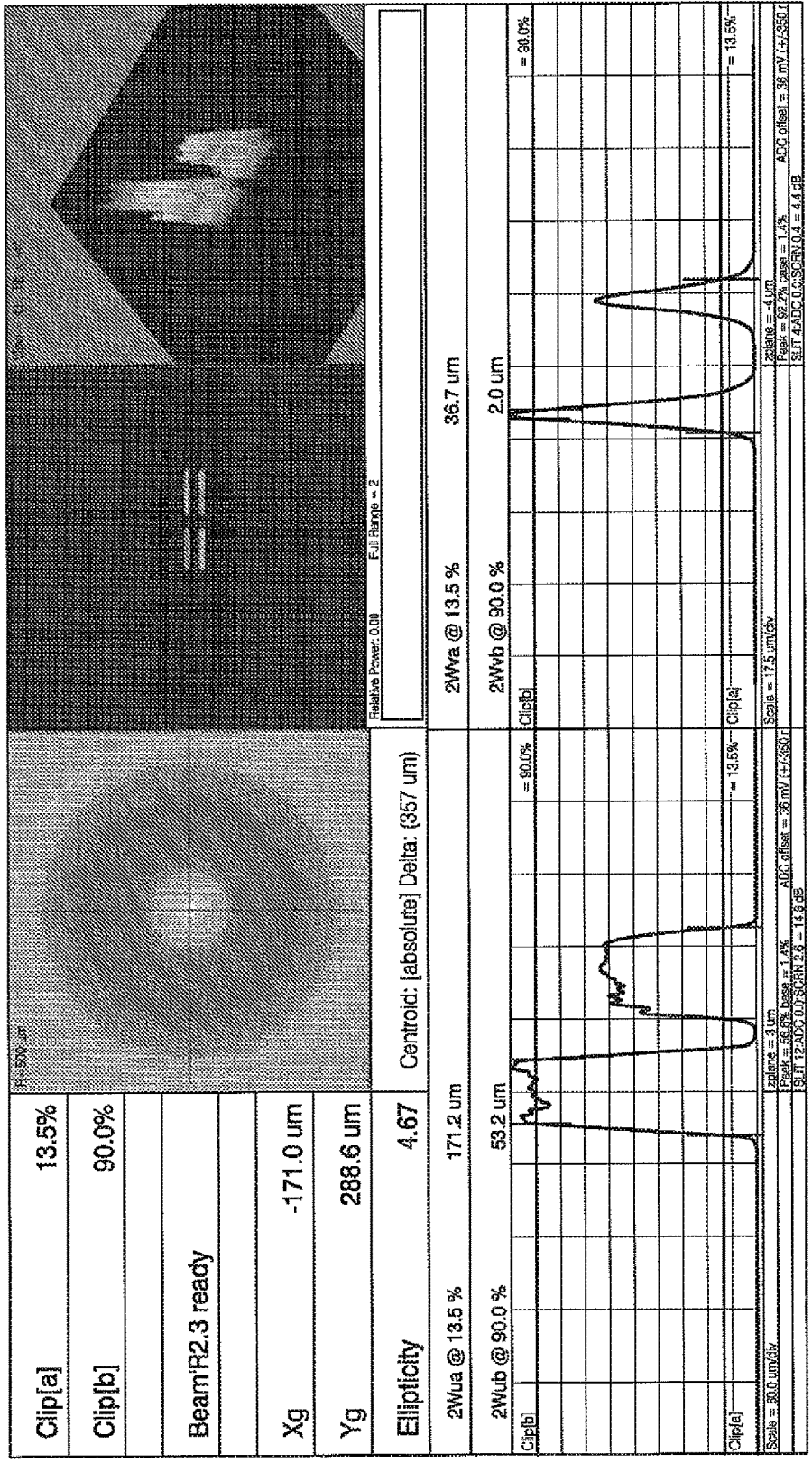
FIG. 8C   Blue and Violet Laser Beam at Focus

Blue Laser Beam at Focus

SYSTEMS, METHODS, AND APPARATUSES FOR OPTICAL SYSTEMS IN FLOW CYTOMETERS

CROSS-REFERENCE TO RELATED APPLICATIONS

This application is a continuation of U.S. application Ser. No. 15/633,613 filed Jun. 26, 2017, now U.S. Pat. No. 10,018,553, which is a continuation of U.S. application Ser. No. 14/607,677 filed Jan. 28, 2015, now U.S. Pat. No. 9,726,593, which claims priority to U.S. application No. 62/041,806 filed Aug. 26, 2014, and U.S. application No. 61/946,579 filed Feb. 28, 2014, which disclosures are herein incorporated by reference in their entirety.

FIELD

The present disclosure generally relates to optical systems in flow cytometers.

BACKGROUND

Flow cytometry is a powerful tool used for analysis of particles and cells in a myriad of applications primarily in bioscience research and medicine. The analytical strength of the technique is in its ability to parade single particles (including bioparticles such as cells, bacteria and viruses) through a focused spot or spots of light, typically from a laser or lasers, in rapid succession, at rates up to thousands of particles per second. The high photon flux at this focal spot produces scatter of light by a particle and or emission of light from the particle or labels attached to the particle that can be collected and analyzed. This gives the user a wealth of information about individual particles that can be quickly parleyed into statistical information about populations of particles or cells.

In flow cytometry, multi-beam, multi-wavelength excitation is commonly used to increase the available number of fluorophores that can act as optical reporters. The increased spectral space allows for a greater degree of assay multi-plexing for individual targets.

Multi-beam flow cytometry can be implemented in several different ways. The simplest is to co-locate beams along the same optical axis. In this situation, multi-plexing is limited by the spectral overlap of fluorophores excited by the wavelength of the co-located beams. In most systems, beams are delivered to the flow cell in a stacked manner with a small distance between beams. This allows for spatially separated interrogation zones for each laser or other type of light. In these systems, the magnitude of the spatial separation is chosen to reduce cross talk between adjacent lasers while minimizing the uncertainty of particle position due to fluctuations of the fluidic system. As spatial separation increases cross talk decreases, but uncertainty of a particle position increases.

Due to system requirements that mandate high particle analysis rates and high illumination intensity, a small laser spot size is desired at a target. In most systems, a converging beam is required to achieve this level of focus on target. A converging beam is typically produced by expanding laser light (e.g., collimating or partially collimating) and then propagating it through a focusing lens. For systems with multiple lasers, the collimated optical beams may be stacked with a displacement of a few hundred microns to produce a final spot separation in that order. The collimated beams are then passed through a single focusing lens, as seen in FIG. 1, and then propagated to the interrogation zone where the particles pass.

The single lens approach has proven effective and has been a mainstay for many decades. Its drawback is that the focusing lens is coupled to all the beams in the system simultaneously. Adjustment of the single focusing lens or implementing other lens manipulations to improve the focus of one beam degrades the focus of adjacent beams. Such a system can produce lower quality data, necessitate more effort in calibrating the focus, and also makes interchangeability of the light sources (e.g. lasers) extremely difficult.

The solution to these drawbacks, as presented herein, is a system in which converging beams can be propagated through the optical train instead of collimated beams without the introduction of aberrations. See FIG. 2. Such a system will allow for adjustment of each laser beam without interfering with the optical path of adjacent lasers beams and allow for improved data and results.

SUMMARY

In one aspect, an optical system for a flow cytometer is disclosed. The optical system can include a flow cell including a particle interrogation zone. The optical system can include at least two optical subunits comprising a light source producing a light beam and a converging element configured to convert the light beam into a converging light beam.

In one aspect, a method to combine light beams in a flow cytometer is disclosed. The method can include providing at least two light beams. The method can include passing each of the light beams through a converging element in a one light beam per converging element ratio wherein the light beams leaving the converging elements are converging light beams. The method can include passing at least one of the converging light beams through at least one dichroic element. The method can include spatially separating the converging light beams from one another upon entering the interrogation zone within a flow cell.

In one aspect, a flow cytometer optical alignment method is disclosed. The method can include producing at least two converging light beams wherein each of the converging light beams is produced by passing a light beam produced by a light source through a converging element wherein the light source and the converging element are affixed to an opto-mechanical mount. The method can include passing at least one of the converging light beams through a dichroic element. The method can include passing each of the converging light beams through a flow cell in a set of spatially distinct first positions. The method can include adjusting at least one of the opto-mechanical mounts to reposition at least one light source and at least one converging element. The method can include passing each of the converging light beams through a flow cell in a set of spatially distinct second positions.

BRIEF DESCRIPTION OF THE SEVERAL VIEWS OF THE DRAWINGS

For a more complete understanding of the principles disclosed herein, and the advantages thereof, reference is now made to the following descriptions taken in conjunction with the accompanying drawings, in which:

FIG. 8A depicts a blue laser system at focus with associated profiles.

FIG. 8C depicts a blue and violet laser system at focus with associated profiles.

Figure 1:
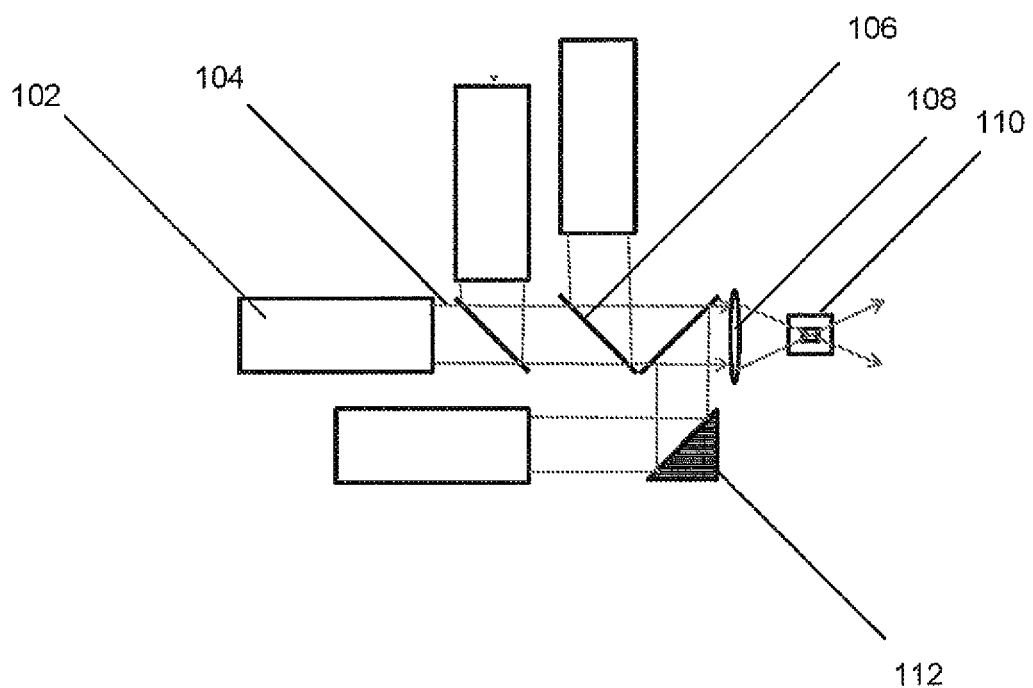
FIG. 1 is an illustration of an optical system for a flow cytometer according to the prior art.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

In order that the present disclosure may be more readily understood, certain terms are first defined. Additional definitions are set forth throughout the detailed description.

DETAILED DESCRIPTION OF THE EMBODIMENTS

Embodiments of systems, methods, and apparatuses for optical systems in a flow cytometer are described in the accompanying description and figures, which includes Exhibit 1. In the figures, numerous specific details are set forth to provide a thorough understanding of certain embodiments. A skilled artisan will be able to appreciate that the optical system described herein can be used in a variety of instruments using optical trains including, but not limited to, flow cytometers. Additionally, the skilled artisan will appreciate that certain embodiments may be practiced without these specific details. Furthermore, one skilled in the art can readily appreciate that the specific sequences in which methods are presented and performed are illustrative and it is contemplated that the sequences can be varied and still remain within the spirit and scope of certain embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

In order that the present disclosure may be more readily understood, certain terms are first defined. Additional definitions are set forth throughout the detailed description.

As used herein "about" means plus or minus 20%, more preferably plus or minus 10%, even more preferably plus or minus 5%, most preferably plus or minus 2%.

As used herein "dichroic" means a wavelength selectively reflective element.

As used herein "flow cell" means a channel, chamber or capillary having an interior shape selected from rectangular, square, elliptical, oblate circular, round, octagonal, heptagonal, hexagonal, pentagonal, and triagonal.

As used herein "channel" means a course, pathway, or conduit with at least an inlet and preferably an outlet that can contain an amount of fluid having an interior shape selected from rectangular, square, elliptical, oblate circular, round, octagonal, heptagonal, hexagonal, pentagonal, and triagonal.

As used herein "particle" means a small unit of matter, to include but not limited to: biological cells, such as, eukaryotic and prokaryotic cells, archaea, bacteria, mold, plant cells, yeast, protozoa, ameba, protists, animal cells; cell organelles; organic/inorganic elements or molecules; microspheres; and droplets of immiscible fluid such as oil in water.

As used herein "analyte" means a substance or material to be analyzed.

As used herein "probe" means a substance that is labeled or otherwise marked and used to detect or identify another substance in a fluid or sample.

As used herein "target" means anything coming into contact with the converging beam.

As used herein "interrogation zone" is the point where the light beam (e.g. a laser) intersects with the particle or the place where the optics system detects light scatter and fluorescence.

As used herein "final focusing lens" means a converging element that is located somewhere in the optical train.

As used herein "fluid stream" means the stream which carries and aligns the particles so that they pass single file through the light beam.

In various embodiments, the optical system disclosed in the present application can be used in conjunction with various apparatuses, systems, and methods relating to flow cytometry. See U.S. patent application Ser. Nos. 12/239,390 and 12/209,084, both of which are incorporated by reference in their entirety.

In flow cytometry, multi-beam excitation is common to increase the available number of fluorophores that can be used as optical reporters. The increased spectral space allows for a greater degree of assay multi-plexing for individual targets. Multi-beam flow cytometry can be implemented in several different ways. The simplest is to co-locate beams along the same optical axis. However, someone skilled in the art will appreciate that interference, spectral overlap and cross-talk will limit the degree of multi-plexing. To reduce this problem beams are delivered to the flow cell in a stacked manner.

Referring to FIG. 1, a schematic of a prior art optical system in the field of flow cytometry is shown. This system is comprised of at least one light source 102 that produces a collimated light beam 104. Prior art systems use plate dichroic elements 106 through which the collimated light beams 104 pass through. The collimated light beam 104 stays collimated as it passes through the dichroic elements 106 in order to be focused at the end of the optical train. One effect of collimation is that it minimizes the introduction of aberrations as the light beam passes through plate dichroic elements 106. If converging beams were used such aberrations would result in poor data quality and are a substantial concern in optical systems such as the ones used in flow cytometry. When the light beam hits a target or particle within the interrogation zone the beam profile has an area commonly referred to as "spot size." Generally, if a light beam can be fit into a smaller space its beam intensity increases which results in higher signal emission relative to the background noise. In order for the spot size of the laser to have a high signal to background noise ratio a converging element 108 is used at the end of the optical train to reduce the spot size of the beam and increase the beam intensity prior to interrogation of a target. As is the case in almost all optical systems, reductions in aberrations and proper focusing are desirable. It is common in flow cytometry to spatially separate (stack) light beams so that a target can be interrogated by different light sources 102 at different times without light sources 102 interfering with one another or creating issues involving cross-talk. The biggest problem with the system as shown in FIG. 1 is several collimated light beams 104 are entering the collimated converging element 108 in a stacked manner and in order to properly focus an individual light beam the converging element 108 may need to be moved. The beams are coupled through the converging element 108 and movement of the lens to adjust one beam could negatively impact the adjustment of adjacent light beams. Additionally, properly calibrating such an optical system can involve several complex lens manipulations and despite best efforts may still result in less than perfect calibration of the optical system. The quality of the resulting data can be poor which can lead to important information not being detectable above the background noise and result in missed data in basic research or improper diagnoses in medical applications.

Figure 2:
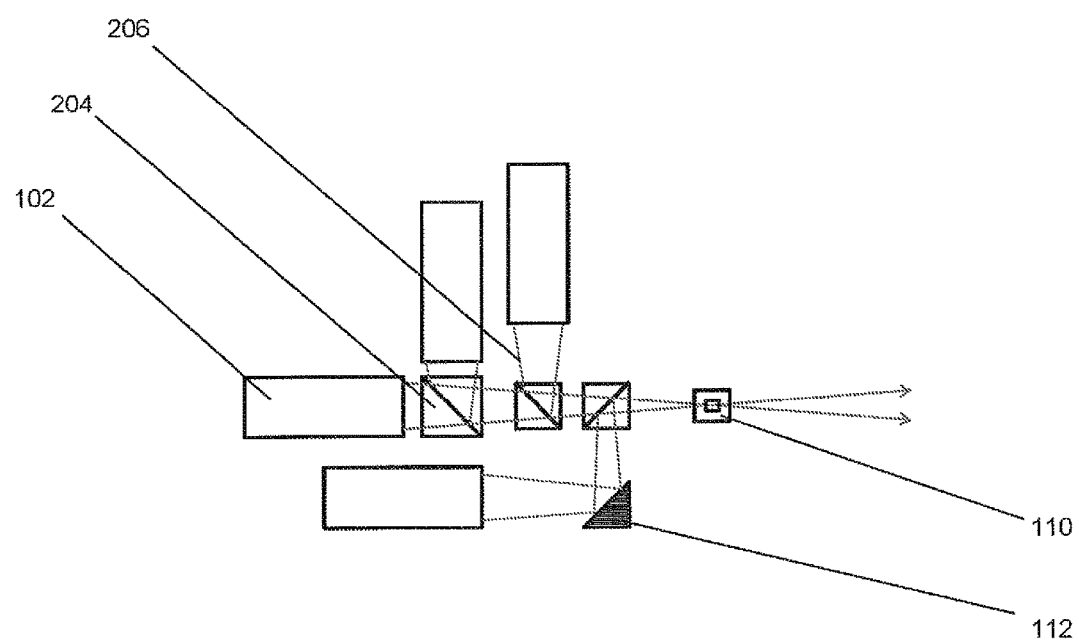
FIG. 2 is an illustration of an optical system for a flow cytometer according to one of the various embodiments.
Figure 3:
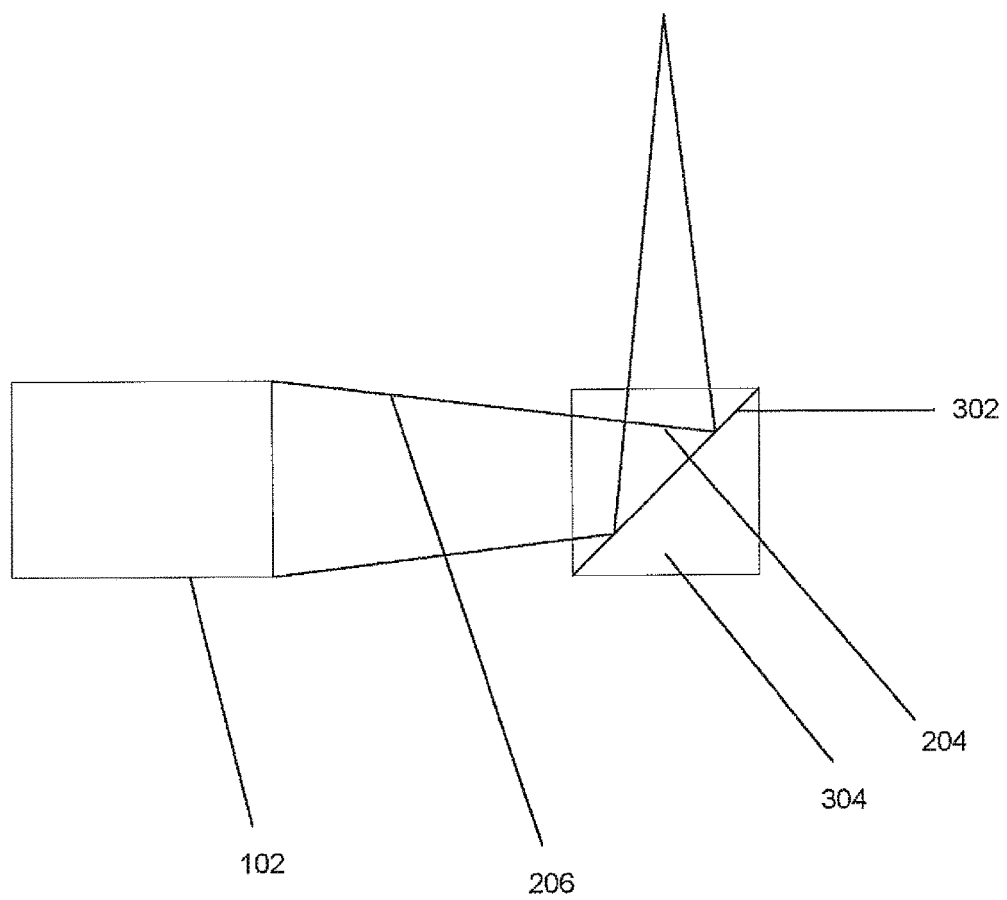
FIG. 3 is an illustration of a close up view of a portion of an optical system for a flow cytometer according to one of the various embodiments.
Figure 5A:
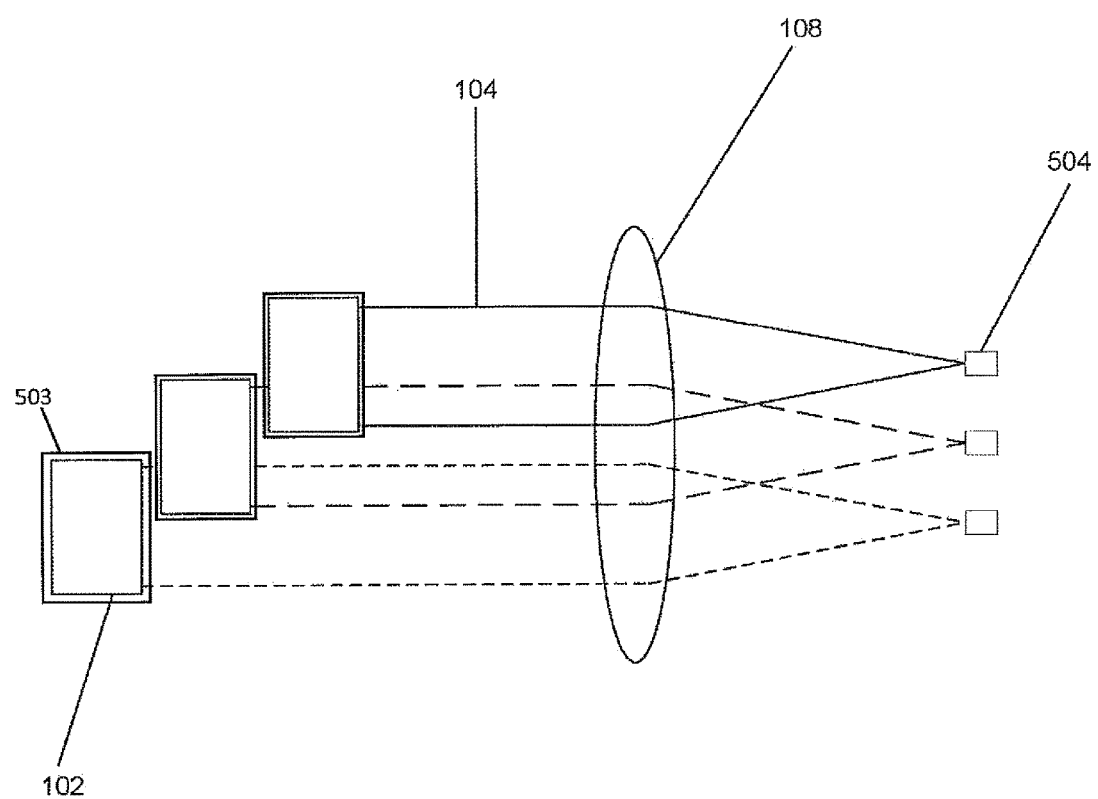
FIG. 5A is an illustration of an optical system for a flow cytometer according to the prior art using collimated beams.
Figure 5B:
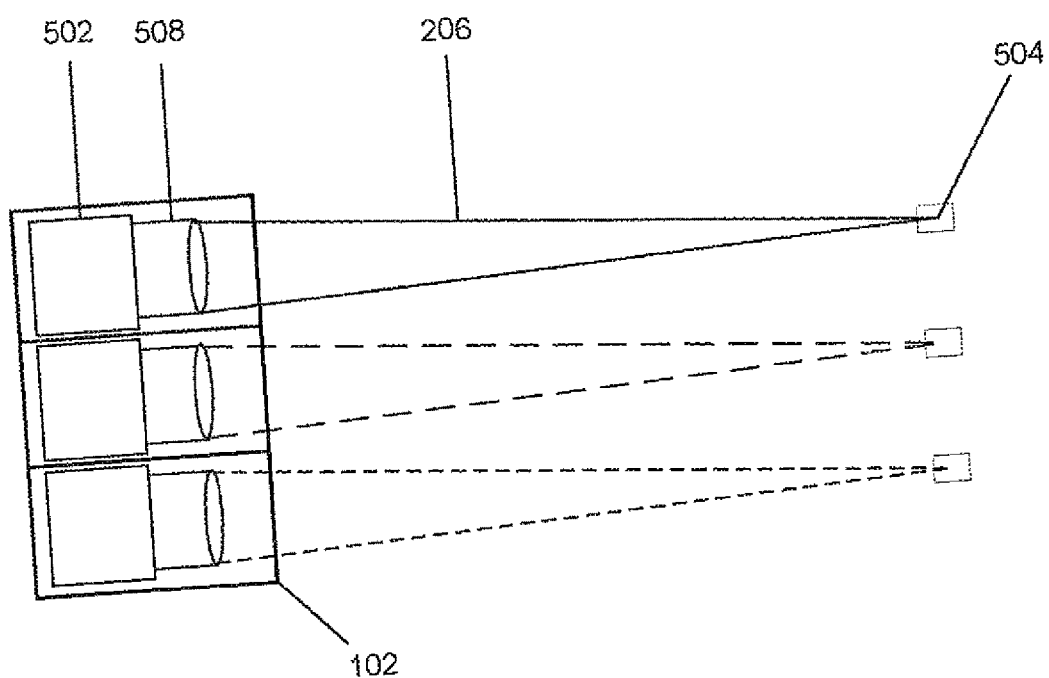
FIG. 5B is an illustration of an optical system for a flow cytometer according to one of the various embodiments using converging beams.

One embodiment of a solution to the problem presented in FIG. 1 is illustrated in FIGS. 2, 3, and 5B where the optical path of each light source 102 can be made independent of the other light sources 102 by moving the final focusing element to the front of the optical path. This distinction can be seen when comparing the location of the converging elements 108 in FIG. 1 and FIG. 5B. Such a system can have one converging element 108 paired with one light source 102. This system makes optical alignment in manufacturing and in the field much simpler by decoupling many of the lens manipulations conducted within each individual light source path. A modular method whereby fully assembled optical subunit 502 with all the optical hardware necessary to produce a converging light beam 206 that focuses to the final spot size can be installed into an instrument or removed and replaced. Alignment of the optical system is then a simple manipulation of the optical subunit 502, whereby, only one optical path can be adjusted at a time. The standard method, FIG. 1, for combining the converging light beams 206 in a stacked or collinear manner would utilize plate dichroic elements 106 to direct the converging light beams 206. But, this would not be possible for the optical setup described above that produces converging light beams 206 at the beginning of the optical path. Aberrations (astigmatism and coma) would be introduced by the plate dichroic elements 106 thereby degrading the final spatial distribution of the laser intensity profile and thereby degrading the performance of the instrument. The aberrations introduced into converging light beams 206 by plate dichroic elements 106 are described in the known art. J. Bratt, *Analytical expressions for the wave front aberration coefficients of a tilted plane-parallel plate*, Applied Optics 36, 8459-8467 (1997). J. van den Eerenbeemd and S. Stallinga, *Compact system description for systems comprising a tilted plane parallel plate*, Applied Optics 46, 319-326 (2007).

As shown in FIG. 1, an optical system for a flow cytometer can include a flow cell 110 and at least two optical subunits 502 as seen in FIG. 5B. The flow cell 110 can include a particle interrogation zone. In general, a light beam can be focused onto an interrogation zone wherein particles can pass through the focused light beam. An optical subunit 502 can comprise a light source 102 and a converging element 108. In various embodiments the light source 102 can produce a substantially monochromatic light beam. In various embodiments the light source 102 can produce polychromatic light beams. The converging element 108 can be configured to convert either monochromatic or polychromatic light into a converging light beam 206. In various embodiments, the converging light beam can focus to a diameter of about ten micrometers. In various embodiments, the converging light beam can focus to a diameter of between about one micrometer and twenty micrometers. In various embodiments, the converging light beam can focus to a diameter of between about fives micrometers and one hundred micrometers. In various embodiments the light beam entering the converging element 108 can either be expanding, converging, or collimated. In various embodiments the optical subunits 502 can be affixed to an opto-mechanical mount. The opto-mechanical mounts can be manipulated by an operator to adjust the spatial separation of the converging light beams 206 or can be manipulated to adjust the focus of the converging light beams 206 within a flow cell 110. Such a system will allow for adjustment of each laser beam without interfering with the optical path of adjacent lasers beams and allow for improved data and results.

In various embodiments, the optical system further comprises at least one dichroic element 204 that is configured to direct the converging light beams 206 to the flow cell 110. The dichroic element 204 can be comprised of two adjoined prisms 304 and a wavelength selective coating 302 located between the adjoined prisms 304. In various embodiments, an element can be used that is trichroic or more and can make use of any number of prisms 304 and any number of wavelength selective coatings 302. In various embodiments, the dichroic element 204 used can be in the shape of a cube. A cube shape can allow for entry faces to be near perpendicular to the incoming beams and the exit faces can be near perpendicular to the transmitted converging light beams 206. In various embodiments, the cube structure can reduce or almost eliminate the introduction of aberrations. In various embodiments, the cube can be constructed by joining two 45 degree prisms 304. In various embodiments, a wavelength selective coating 302 can be placed on the adjoining surface between the prisms 304. Because the propagation of a converging wave front through a cube allows for fewer and less pronounced aberrations in the converging light beam 206, it is not necessary to propagate collimated light beams 104 through the dichroic cube. In various embodiments, the final focusing lens (e.g. the converging element 108 in FIG. 5B) in a multi-laser system can be relocated earlier in the optical path where it can be decoupled from the other optical axes. In such embodiments, the lens assemblies with independent converging elements 108 can be mounted on a three axis opto-mechanical mount with independent mechanical adjustments for aiming and focusing the converging light beam 206. In various embodiments, the location of each beam waist and position can be individually adjusted for each converging light beam 206 without affecting the focus of the other converging light beams 206. Such configurations also eliminate issues caused by chromatic and spherical aberrations that are compounded when several beams of different wavelengths are propagated through the same collimated converging element 108 and having the requirement to focus in the same plane. In the various embodiments using dichroic cubes (or other geometries with similar properties), a converging light beam 206 configuration of multiple light sources 102 can be constructed where the adjustment of the optical components of each light beam optical path are decoupled. Additionally, such embodiments allow for the creation a modular flow cytometer. In the various embodiments that decouple the light beam lines, adding additional light beams lines does not require having to adjust coupled optical components. Such embodiments are especially advantageous in the field in and manufacturing environments.

The combination of at least two optical subunits 502 and at least one dichroic element 204 has not been practiced before. One reason could be the increased cost of dichroic elements 204 in the form of cubes or other geometries versus plate dichroic elements 204 which contain much less material. Additionally, optical subunits 502 are more complicated to produce.

In various embodiments the wavelength selective coating 302 acts as a long pass filter. In other embodiments the wavelength selective coating 302 acts as a short pass filter. In additional embodiments, mirror elements 112 can be used in the various embodiments of the present optical system.

In various embodiments, the opto-mechanical mounts can be adjusted on an x, y, and z coordinate system. Placing the optical subunits 502 on opto-mechanical mounts 503 can allow adjustment of each light source 102 independent of other light sources 102 being used to create the proper focus and spot size with fewer and less pronounced aberrations required for the particular application. Plate dichroic elements 106 have been used in the past because they work very well for the majority of applications at a reduced cost. However, the various embodiments of the present system are superior to that of a plate dichroic system transmitting collimated light beams 104 for the above described reasons.

In various embodiments, a particle moves through the flow cell 110. In such embodiments, the particle can be interrogated by each of the converging light beams 206 independently.

In various embodiments, the converging element 108 can be a convex lens.

In various embodiments, the spatial separation can be between about 80 micrometers to about 200 micrometers when passing through the interrogation zone. In various embodiments, the spatial separation can be between about 10 micrometers to about 100 micrometers. In various embodiments, the spatial separation can be about 150 micrometers.

In various embodiments, the converging light beam 206 can have a flat top intensity profile. In various embodiments, the converging light beam 206 can have a Gaussian intensity profile. In various embodiments, the intensity profile can be altered depending on the application.

Figure 4:
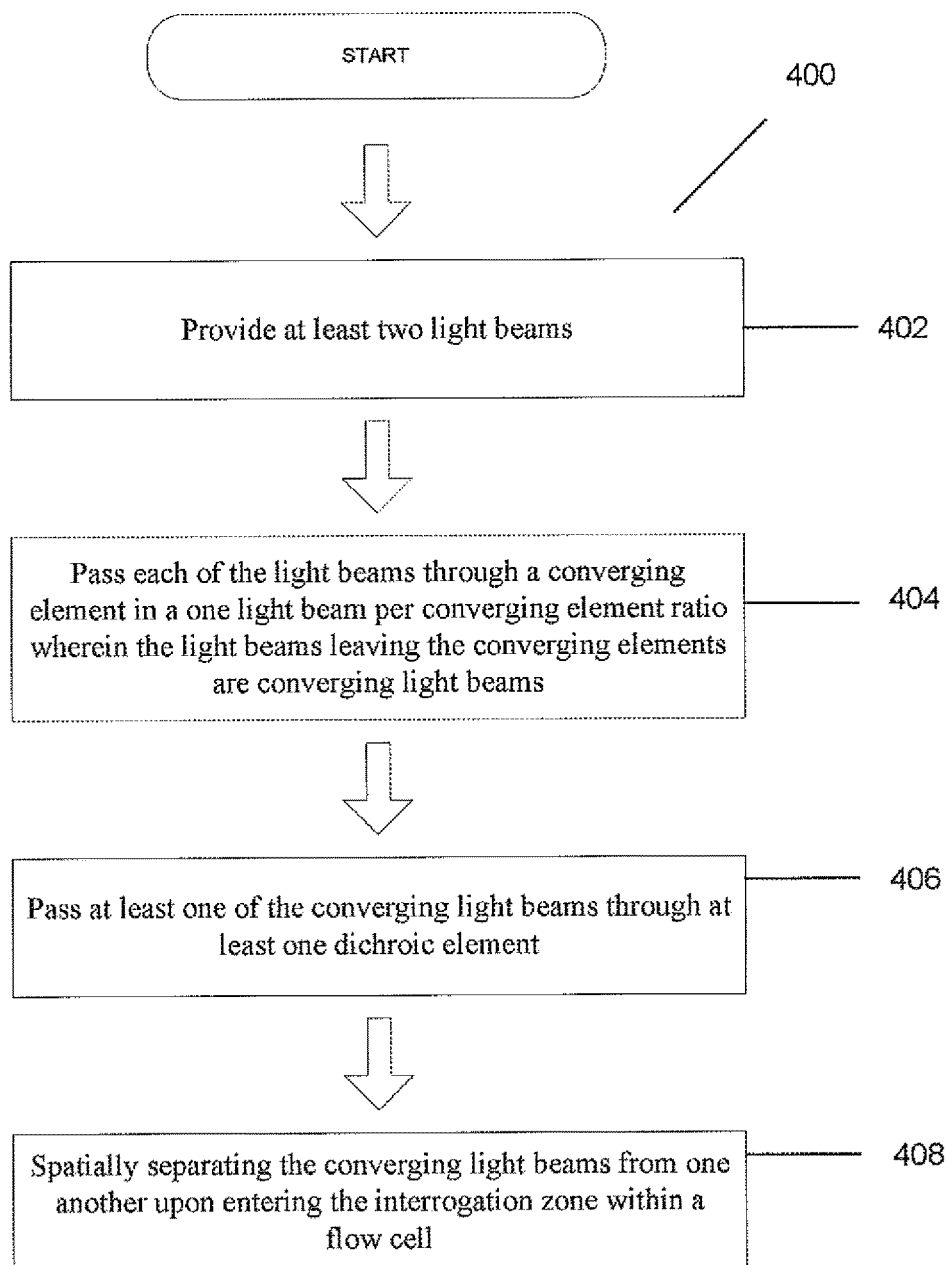
FIG. 4 illustrates a flow diagram according to one of the various embodiments.

FIG. 4 is an exemplary flowchart showing a method 400 for flow cytometer optical alignment, in accordance with various embodiments.

In step 402, at least two light beams can be provided. In step 404, each of the light beams can be passed through a converging element in a one light beam per converging element ratio wherein the light beams leaving the converging elements can be converging light beams 206. In step 406, at least one of the converging light beams 206 can be passed through at least one dichroic element 204. In step 408, the converging light beams 206 can be spatially separated from one another upon entering the interrogation zone within a flow cell 110.

In various embodiments of the method, the light beams can be monochromatic light emissions and can be produced by the light source 102. In various embodiments, the light source 102 and the converging element 108 can be affixed to an opto-mechanical mount. In various embodiments, the opto-mechanical mount can be adjusted on an x, y, and z coordinate system. In various embodiments, a further step can include replacing a first light source 102 configured to produce a monochromatic light emission with a first wavelength with a second light source 102 configured to produce a monochromatic light emission with a second wavelength.

In various embodiments of the method, the dichroic element 204 can be configured to prevent introduction of aberrations into the converging light beams 206. In various embodiments, the dichroic element 204 can be in the shape of a cube. In various embodiments, the dichroic elements 204 can be long pass filters or short pass filters. In various embodiments, a further step can include replacing at least one first dichroic element 204 configured to pass a first range of wavelengths with at least one second dichroic element 204 configured to pass a second range of wavelengths.

In various embodiments of the method, the adjustment of the opto-mechanical mounts can occur on an x, y, and z axis.

In various embodiments of the method, a further step can include interrogating a particle wherein the particle is passing through the flow cell 110 in a fluid stream. In various embodiments, the fluid can be a liquid. In various embodiments, a further step can include detecting light scatter with a detection element. In various embodiments, the detection element can comprise a photo multiplier tube. In various embodiments there can be forward and side scattered light generated when the converging light beam 206 strikes the target. In various embodiments, side scattered light can pass through a detection lens and then enter a pinhole collection fiber array wherein each pinhole can correspond to a specific converging light beam 206 that has entered the flow cell 110 in a spatially separated manner. In various embodiments the spatial separations can range from about 80 micrometers to about 200 micrometers. In various embodiments, the spatial separation can be between about 10 micrometers to about 100 micrometers. In various embodiments, the spatial separation can be about 150 micrometers. In various embodiments, fiber optic cables can connect the light coming out of each pinhole to a collection block. In various embodiments a collection block can include collimators, filter elements, and photo multiplier tubes. In various embodiments the signal can be converted from analog to digital data which can then be stored and analyzed on a computer. In various embodiments, forward scattered light can pass a blocker bar, condenser lens, and be converted from analog to digital data signal. In various embodiments, the digital data signal can then be stored and analyzed on a computer.

In various embodiments, a further step can include applying hydrodynamic and or acoustic focusing to the particle.

In various system, apparatus, and method embodiments, an optical subunit 502, a dichroic element 204, and collection block can be associated with a first wavelength of light. In various embodiments, the optical subunit 502, the dichroic element 204, and the collection block described above can be removed from the rest of the flow cytometer system and then replaced with a different optical subunit 502, dichroic element 204, and collection block that are associated with a second wavelength of light. In various embodiments, the computer where the digital data is stored can be programmed with this change in optical components and then analyze data using a new set of parameters.

In various embodiments of the method, the dichroic element 204 can be configured to prevent introduction of aberrations into the converging light beams 206. As previous discussed, plate dichroic elements 106, as seen in FIG. 3, introduce aberrations into converging light beams 206, but not collimated light beams 104. In various embodiments, the dichroic element 204 can be in the form of a cube which can allow all parts of the converging light beams 206 to enter the cube at the same time which then allows the converging light beams 206 to enter a new medium with a different index of refraction with little or no introduction of aberrations. In this configuration, the exiting converging light beams 206 can enter air or another medium from which they originated without the introduction of aberrations on the back end as well.

In various embodiments of the method, the converging light beams 206 can have a flat top intensity profile. Such a flat top intensity profile can allow for uniform interrogation of a target whether that target is a particle, cell, bead, or other.

Now referring to FIG. 5A and FIG. 5B, a further comparison of prior art and the present disclosure are illustrated. In FIG. 5A light sources 102 can be seen producing collimated light beams 104. After some light beam manipulations occur (not shown) the collimated light beams 104 pass through a converging element 108 and then strike a target 504. In this illustration there are three light beams all passing through a single converging element 108. Each light beam must be focused by moving the converging element 108. It is apparent in this illustration that focusing one light beam by changing the position of the converging element 108 will impact the other two light beams because all three light beams pass through the same converging element 108. Such a system is inferior to the system seen in FIG. 5B.

FIG. 5B depicts one example embodiment of an optical system for a flow cytometer. In FIG. 5B, each converging light beam 206 can be produced from an optical subunit 502 containing both a light source 102 and a converging element 108. In such a system, an optical subunit 502 can be mounted to an opto-mechanical mount (not shown) to focus and adjust a converging light beam 206. Such a system can allow for adjustment, commonly focus or spot size, for each converging light beam 206 independent of other converging light beams 206. Such a system provides higher data quality, easier configuration, and modularity as detailed throughout this specification.

The following examples are offered to illustrate, but not limit, the embodiments disclosed herein.

Example 1

Figure 6A:
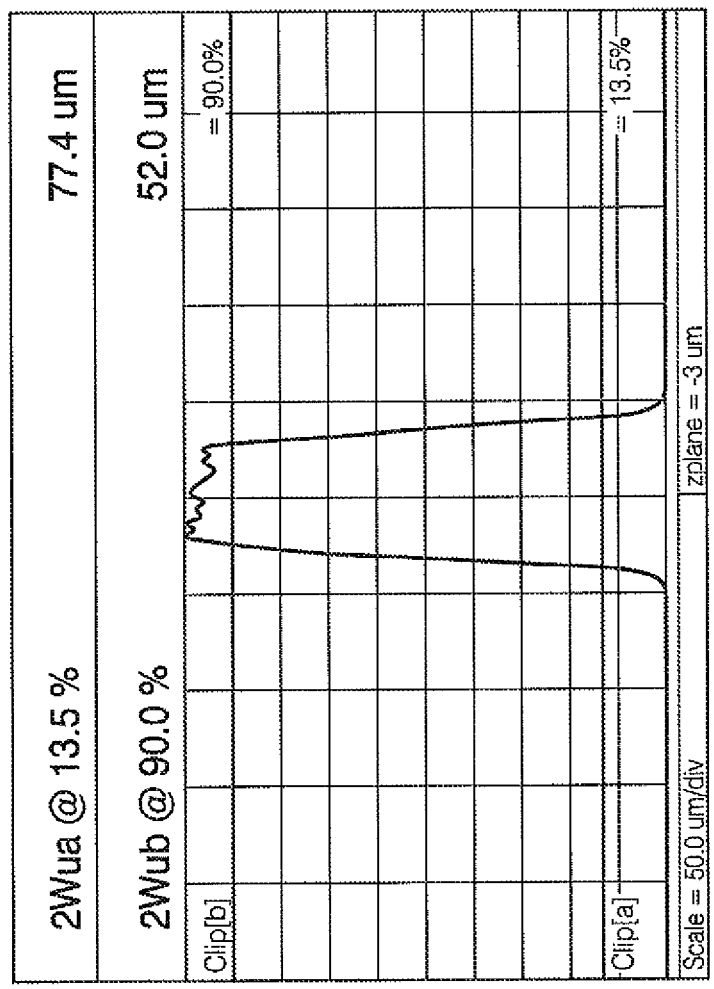
FIG. 6A is a profile of flat top converging laser beams when zero flat plate dichroics are utilized.
Figure 6B:
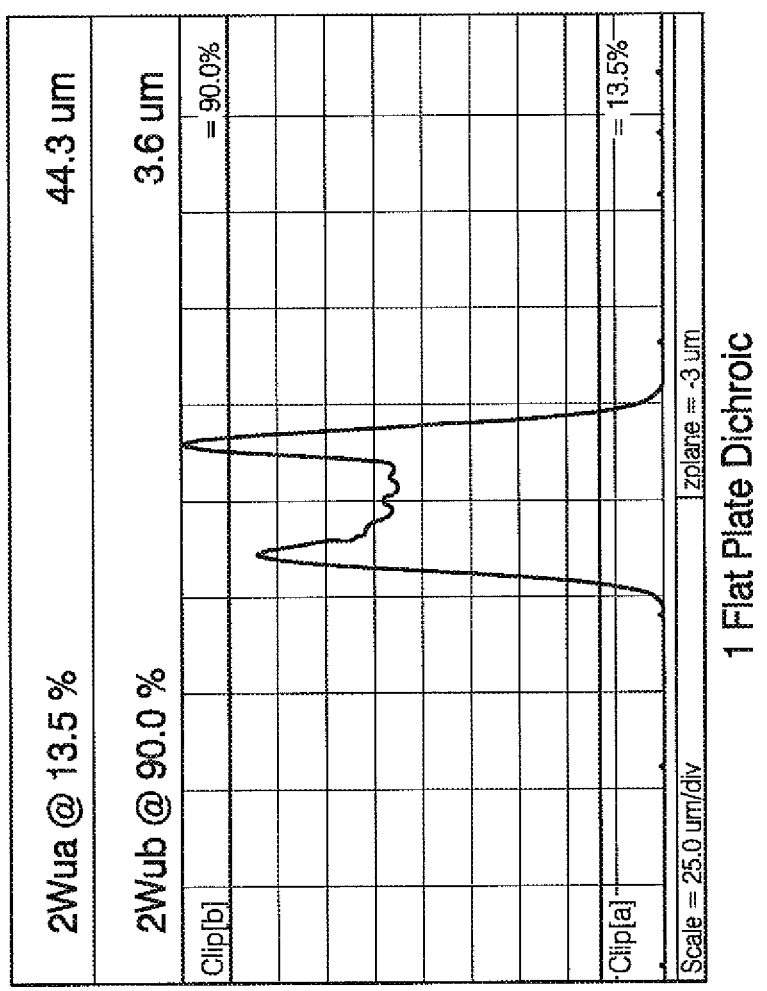
FIG. 6B is a profile of flat top converging laser beams when one flat plate dichroics are utilized.
Figure 6C:
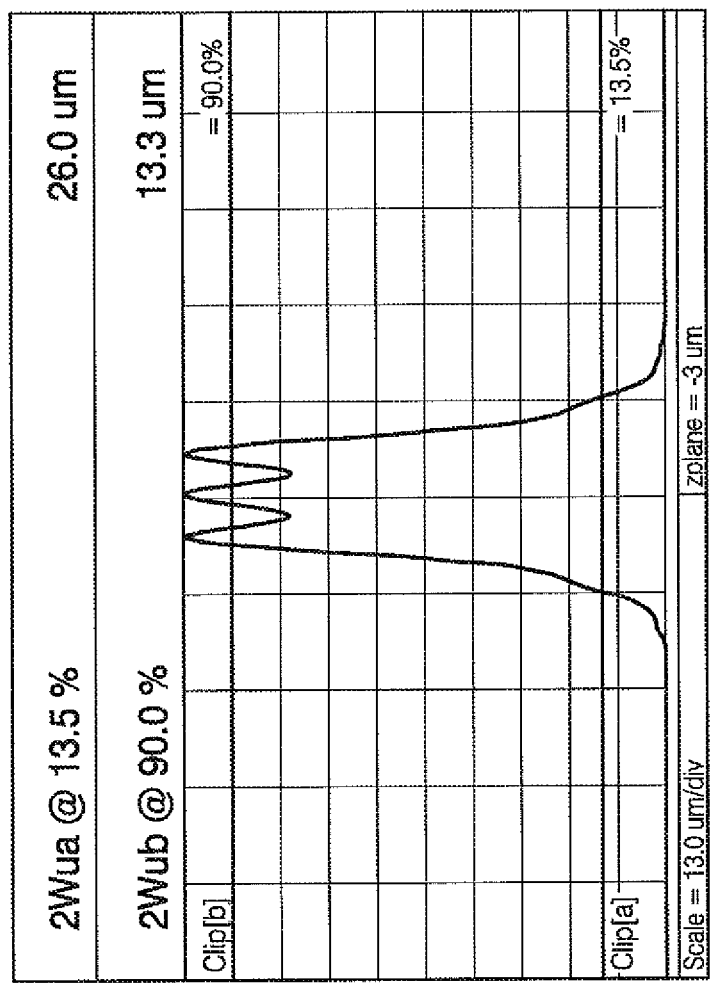
FIG. 6C is a profile of flat top converging laser beams when two flat plate dichroics are utilized.
Figure 6D:
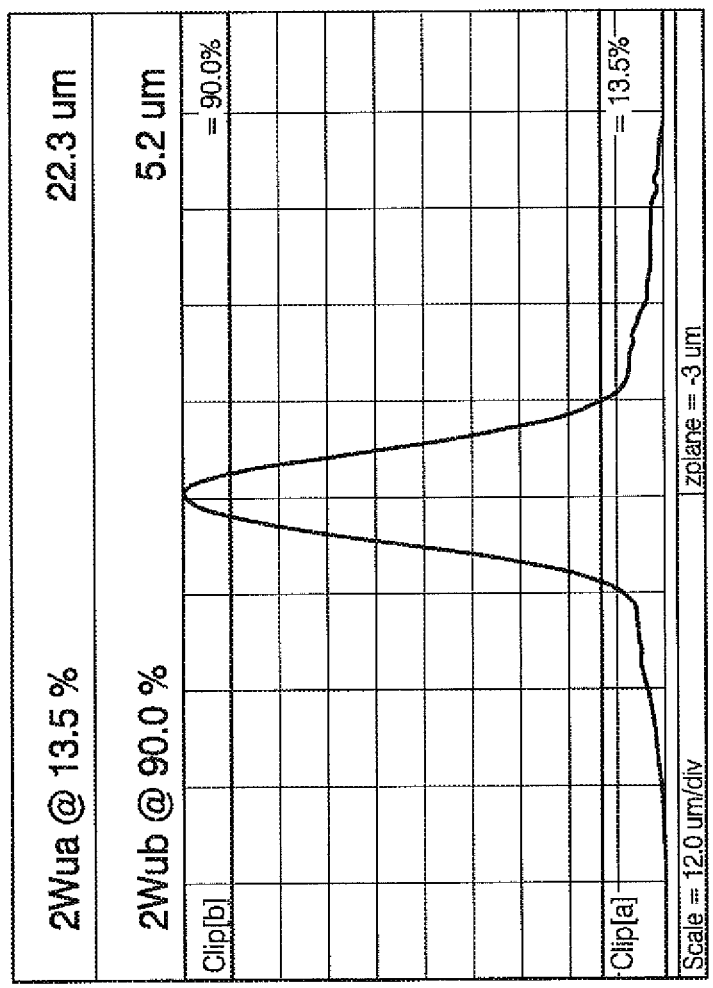
FIG. 6D is a profile of flat top converging laser beams when three flat plate dichroics are utilized.

Flat-Top, Converging Laser Beam Profile Changes When Passing Through Flat Plate Dichroics Set at a 45 Degree Angle Converging laser beams were passed through between 0 and 3 flat plate dichroics (FIGS. 6A-6D) and the resulting beams were imaged by a camera. The x-axis represents beam position and the y-axis represents beam intensity. Intensity on the y-axis has been normalized to 1 (or 100%) where 1 is the highest intensity reached. For most applications, the beam width should be about 50 micrometers across at the 90%. In various embodiments, the beam width can be about 40 micrometers across or about 10 micrometers across while maintaining a beam intensity of at least about 90%. In various embodiments, the beam intensity should be at least about 80%, at least about 70%, at least about 60%, or at least about 50%, while maintaining a beam width of at least about 50 micrometers across. The optimal beam can be seen when 0 dichroic plates (FIG. 6A) are used, but when even 1 flat plate dichroic (FIG. 6B) is added conditions for optimum interrogation of a particle are not met.

This example illustrates that combining the converging light beams 206 technology with plate dichroic elements 106 technology is not optimal. As discussed above, converging light beams 206 allow for the production of independent optical trains. Therefore, another technology (e.g. dichroic elements in the form of prisms) had to be incorporated into these various embodiments.

Example 2

Figure 7A:
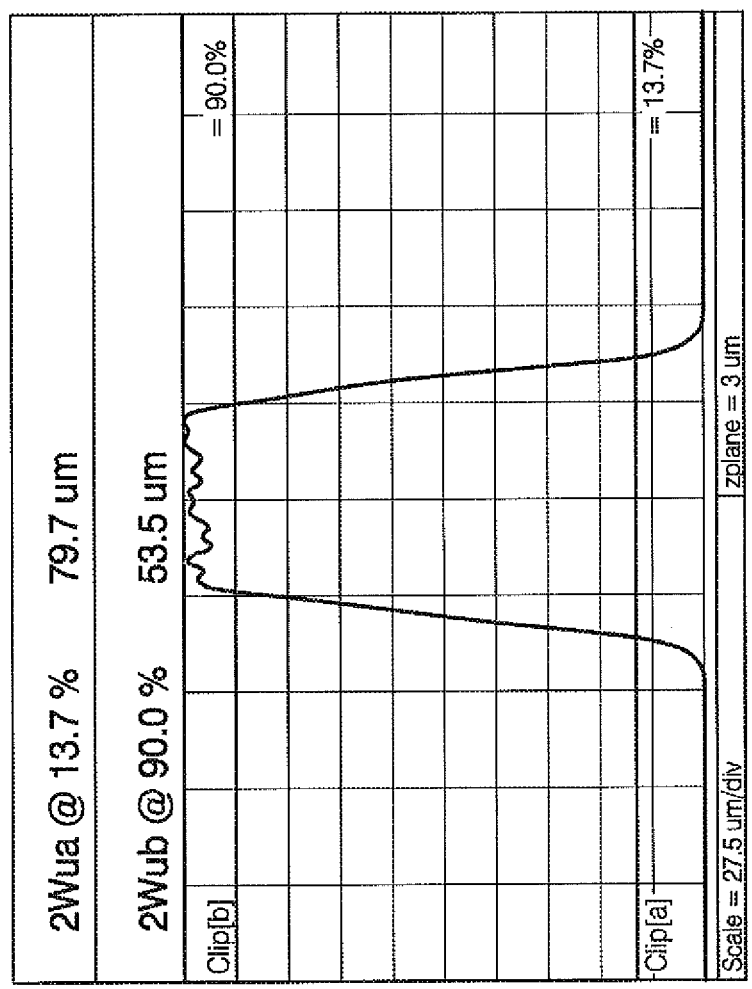
FIG. 7A is a profile of flat top converging laser beams when zero cube dichroics are utilized.
Figure 7B:
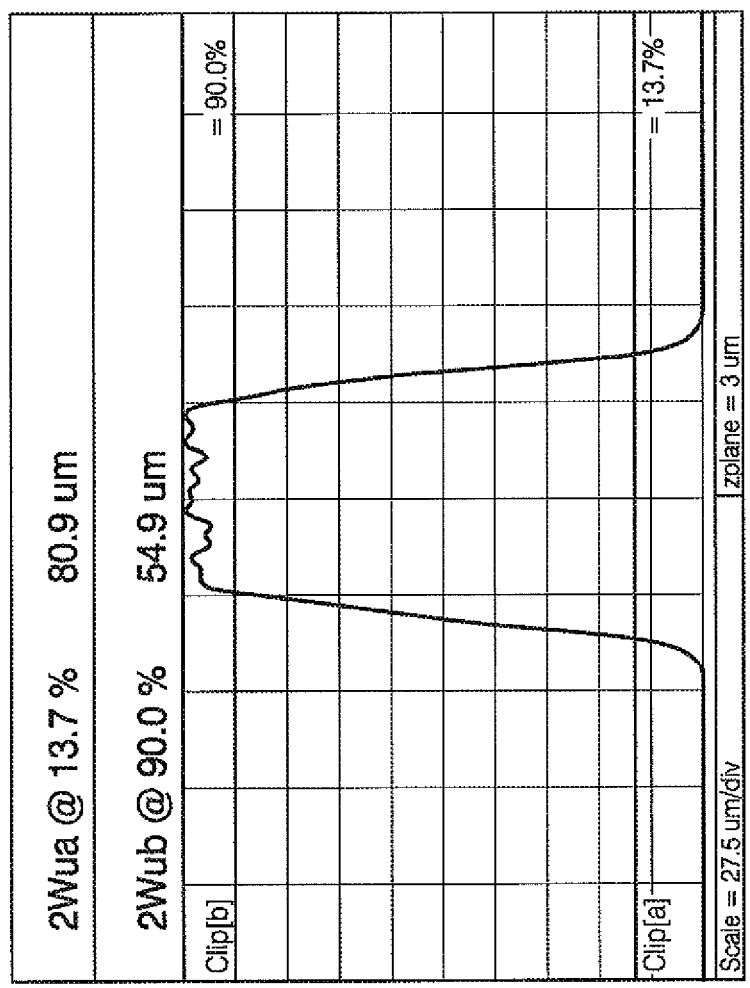
FIG. 7B is a profile of flat top converging laser beams when one cube dichroic are utilized.
Figure 7C:
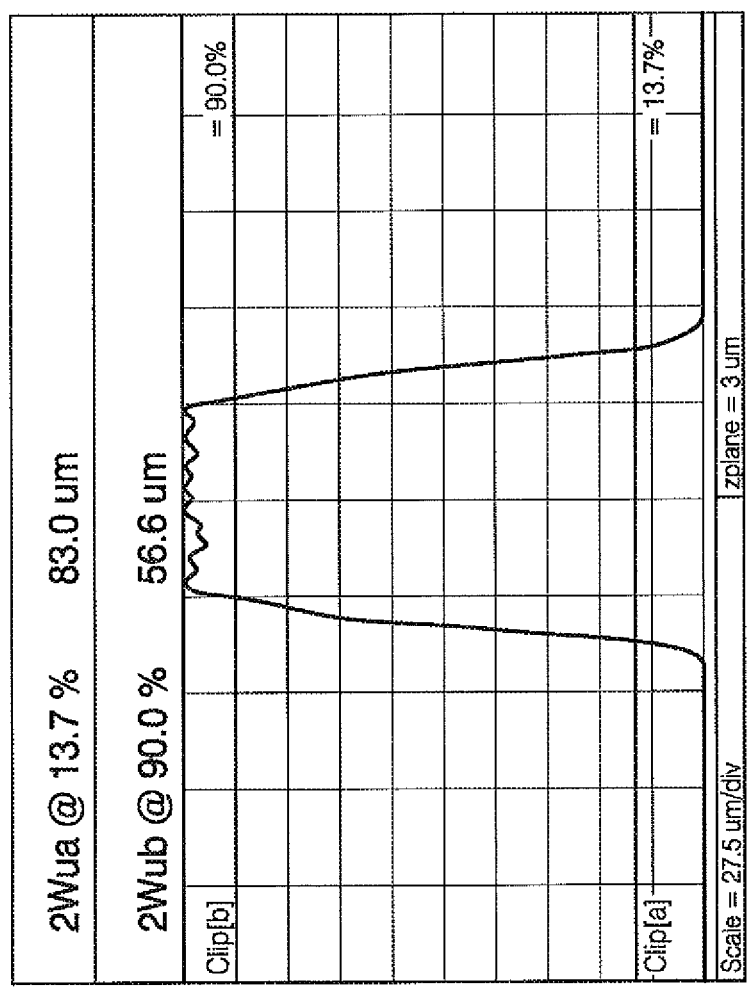
FIG. 7C is a profile of flat top converging laser beams when two cube dichroics are utilized.

Flat-Top, Converging Laser Beam Profile Changes When Passing Through Cube Shaped Dichroics Converging laser beams were passed through between 0 and 2 cube dichroics (FIGS. 7A-7C) and the resulting beams were imaged by a camera. The x-axis represents beam position and the y-axis represents beam intensity. Intensity on the y-axis has been normalized to 1 (or 100%) where 1 is the highest intensity reached. For optimum interrogation conditions the beam width should be about 50 micrometers across and at least about 90% intensity level or higher. 50 micrometers was chosen because the area allows for a high enough beam intensity to be effective while maximizing spot size. The optimal beam can be seen when 0, 1, or 2 dichroic cubes are used.

This example demonstrates a dichroic solution that is compatible with converging light beams 206. Unlike Example 1, there is almost no degradation in the beam profile which can allow for the production of independent optical paths.

Example 3

Wavefront Aberration for a Dichroic Plate Set at a 45 Degree Angle

| Coefficient | Value (1/π) | Aberration |
| --- | --- | --- |
| W40 | 0.0431 | Lowest Order Spherical Aberration |
| W60 | 0.0004 | Sixth Order Spherical Aberration |
| W22 | 2.2018 | Lowest Order Spherical Aberration |
| W42 | −0.0204 | Fifth Order Astigmatism |
| W31 | −0.7685 | Third Order Linear Coma |
| W51 | −0.0065 | Fifth Order Linear Coma |
| W33 | −0.0443 | Cubic Coma |

T=1 mm; n=1.5145; λ=637 nm; pupil radius=9 mm; tilt=45 deg; r=1

$$\Delta W = \sum_l \sum_m W_{lmp} \rho^l \cos m\varphi$$

Example 3 presents well known calculations demonstrating why using dichroic plates in a converging light (e.g. laser) system produce unacceptable beam profiles with significant astigmatism and coma aberrations. Such aberrations reduce the quality of data substantially. T=thickness of the plate used; n=index of refraction; λ=wavelength of light; pupil radius=spot size on glass where calculation is occurring; tilt=angel of plate; and r=distance from the optical axis (exit of pupil radius).

Example 4

Wavefront Aberration for a Dichroic Cube

| Coefficient | Value (1/π) | Aberration |
| --- | --- | --- |
| W40 | 0.6345 | Lowest Order Spherical Aberration |
| W60 | 0.0094 | Sixth Order Spherical Aberration |
| W22 | 0.000 | Lowest Order Spherical Aberration |
| W42 | 0.000 | Fifth Order Astigmatism |
| W31 | 0.000 | Third Order Linear Coma |
| W51 | 0.000 | Fifth Order Linear Coma |
| W33 | 0.000 | Cubic Coma |

T=20 mm; n=1.5145; l=637 nm; pupil radius=9 mm; tilt=0 deg; r=1

See Above for Equation

Example 4 presents well known calculations that demonstrate that using dichroic cubes in place of dichroic plates results in no coma or astigmatism. These reductions lead to much higher quality data as compared to an instrument that incorporates converging light (e.g. laser) beams into a dichroic plate optics system.

Example 5

Co-Plannar Focus

The data in Example 5 presents the use of two optical subunits each comprising a light source and a converging element being focused independently without the use of a final focusing lens. The subunits in this example include an opto-mechanical mount that can be spatially adjusted. More specifically, the light sources in the above example are a blue laser and a violet laser. The focusing occurred through use of the optical subunits which is discussed in greater detail throughout the current disclosure.

FIG. 8A, entitled "Blue Laser Beam at Focus", is a two laser system where a blue laser beam has been focused into a camera independently of a violet laser beam which has been blocked with a blocking device. For optimal interrogation conditions within a flow cytometer the beam width is about 50 micrometers across at least about 90% intensity level or higher. The Gaussian focus is about 2 micrometers. Laser beam profile and focusing can have different optimal configurations depending on the application.

Figure 8B:
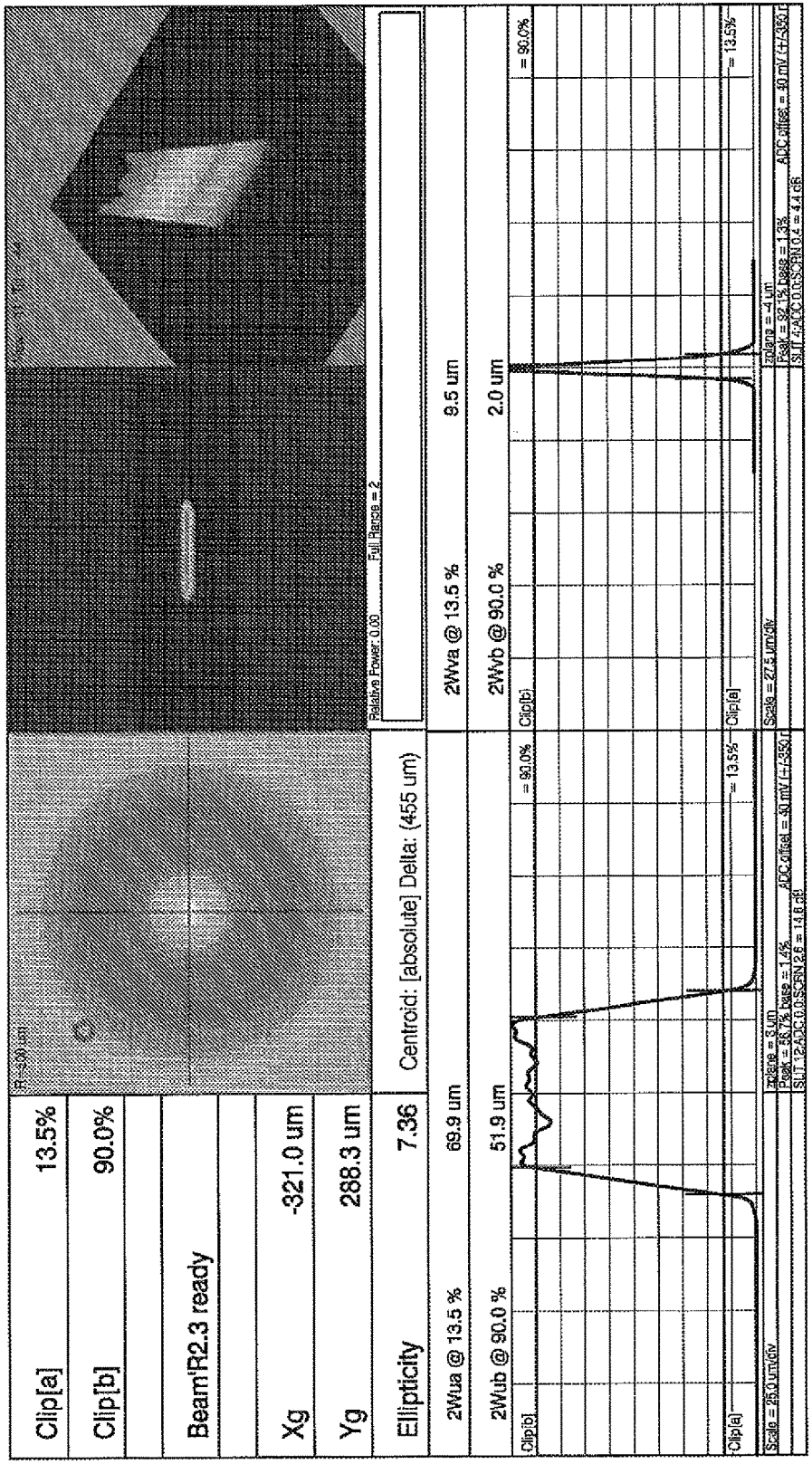
FIG. 8B depicts a violet laser system at focus with associated profiles.

FIG. 8B, entitled "Violet Laser Beam at Focus", is the same two laser system where a violet laser beam has been focused into a camera independently of a blue laser beam which has been blocked with a blocking device. For optimal interrogation conditions within a flow cytometer the beam width is about 50 micrometers across at least about 90% intensity level or higher. The Gaussian focus is about 2 micrometers. Laser beam profile and focusing can have different optimal configurations depending on the application.

FIG. 8C, entitled "Blue and Violet Laser Beams at Focus", presents data demonstrating that both laser beams and their beam shaping optics have been focused independently using optical subunits which includes an opto-mechanical mount system. The lower left portion showing the flat top laser beam profiles has been normalized to the blue laser beam which is why the violet laser beam shows a beam intensity that doesn't span the height of the graph. However, it is shown that about 90% of each laser's intensity occurs over a beam width of about 50 micrometers after each subunit has been adjusted independently. The Gaussian focus for each laser beam is about 2 micrometers. Such adjustment using a final focusing lens, as used in the prior art, would not allow for independent adjustment to focus each laser beam. The detractor of a final focusing lens is that while optimizing one laser beam profile the user may be reducing the optimization of another laser beam profile. Such a problem does not occur in a system where independent beam profile optimization is possible.

Example 6

Reduced Aberration Beam Stacking

Example 6 compares the amount and severity of aberration introduced into an optical system when a laser beam is passed through a 45 degree flat window (e.g. a dichroic plate) with a width of 3 mm versus a dichroic cube element, two dichroic cubes, or through no optical elements.

Figure 9A:
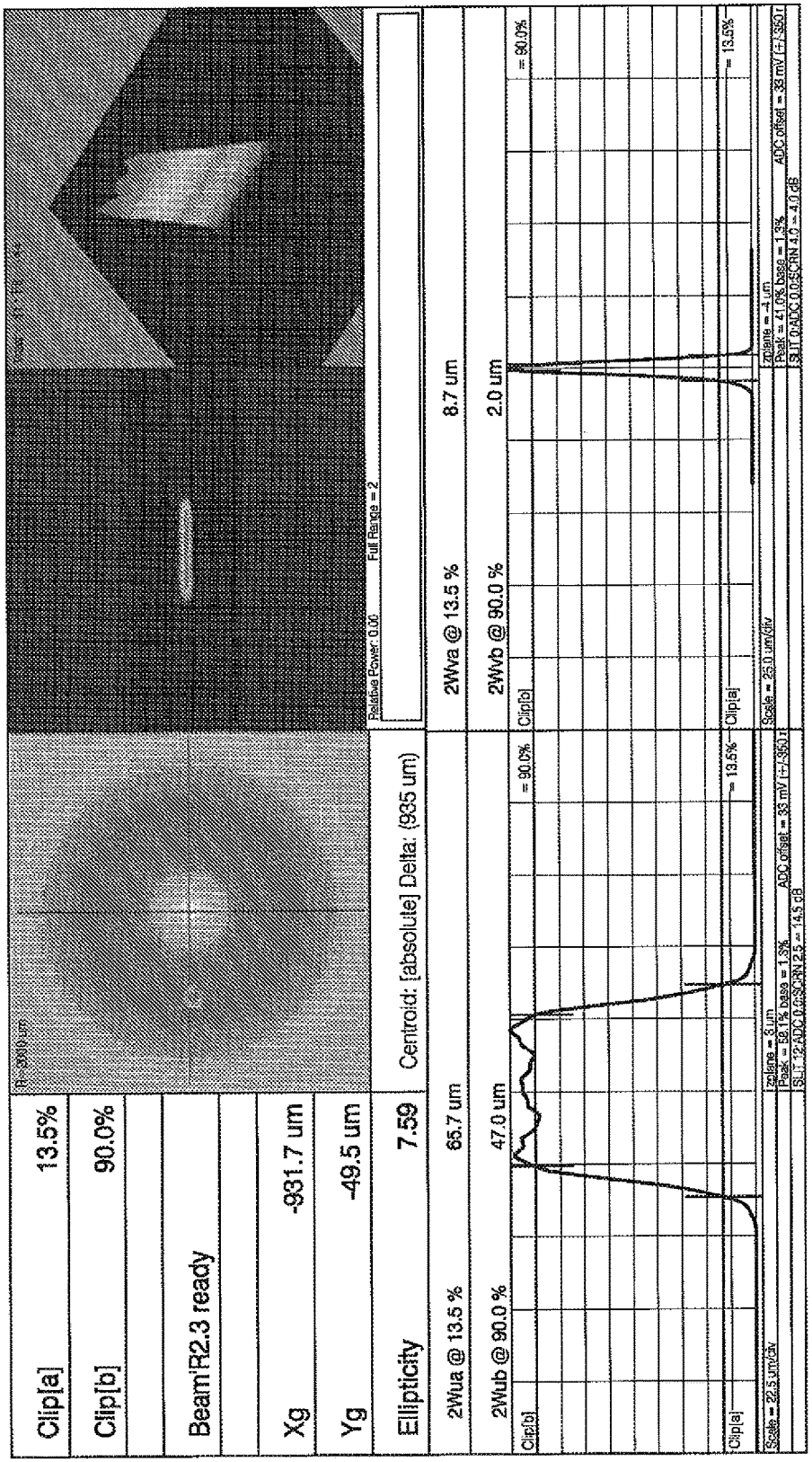
FIG. 9A depicts a blue laser system at focus with associated profiles.

FIG. 9A, entitled "Blue Laser Beam at Focus", shows a blue laser beam focused into a camera without the use of any dichroic elements. Data from a flat top beam is presented in the lower left graph with about 90% of the beam intensity covering a flat top width of about 47 micrometers. The focus is at about 2 micrometers on the Gaussian axis.

Figure 9B:
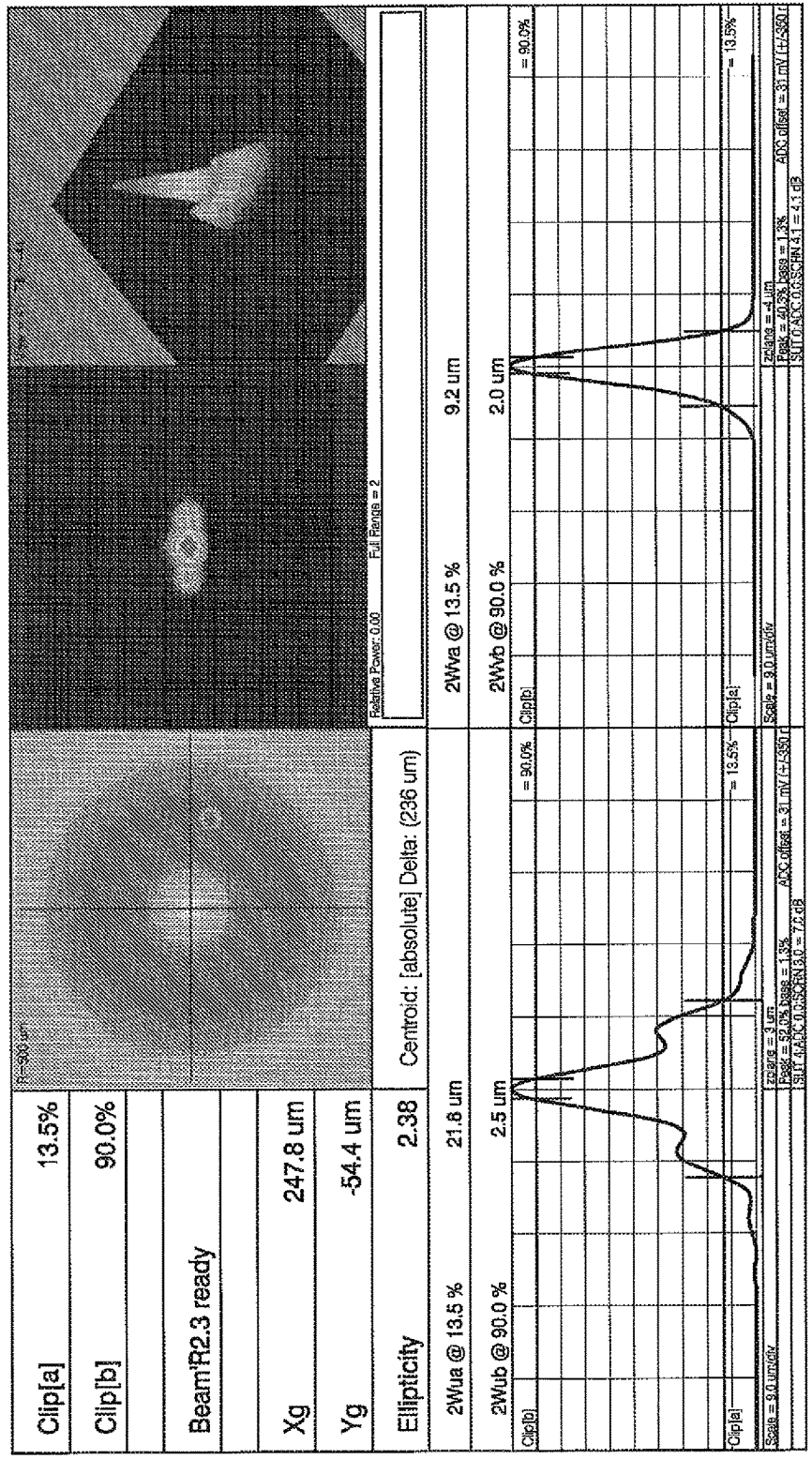
FIG. 9B depicts a blue laser system, with a glass window at 45 degrees, at Gaussian focus with associated profiles.

FIG. 9B, entitled "Blue Laser Beam with a 3 mm 45 Degree Window—At Gaussian Focus", presents data from a blue laser beam focused at a camera with a glass window titled at about 45 degrees incident to the laser beam between the laser source and camera. The glass window is about 3 millimeters thick and constructed from glass. The focus is at about 2 micrometers on the Gaussian axis. The lower left graph shows that there is no longer a flat top beam profile and that only about 2.5 micrometers of the beam width goes above about 90% beam intensity. The difference between this data and the data from the first figure is due to introduction of aberrations from passing the laser beam through the optical element. Such an optical configuration is not suitable for a variety of instruments requiring specific optical conditions, including flow cytometry. When a beam profile takes on the characteristic shown in this figure an abundance of noise is created within the data.

Figure 9C:
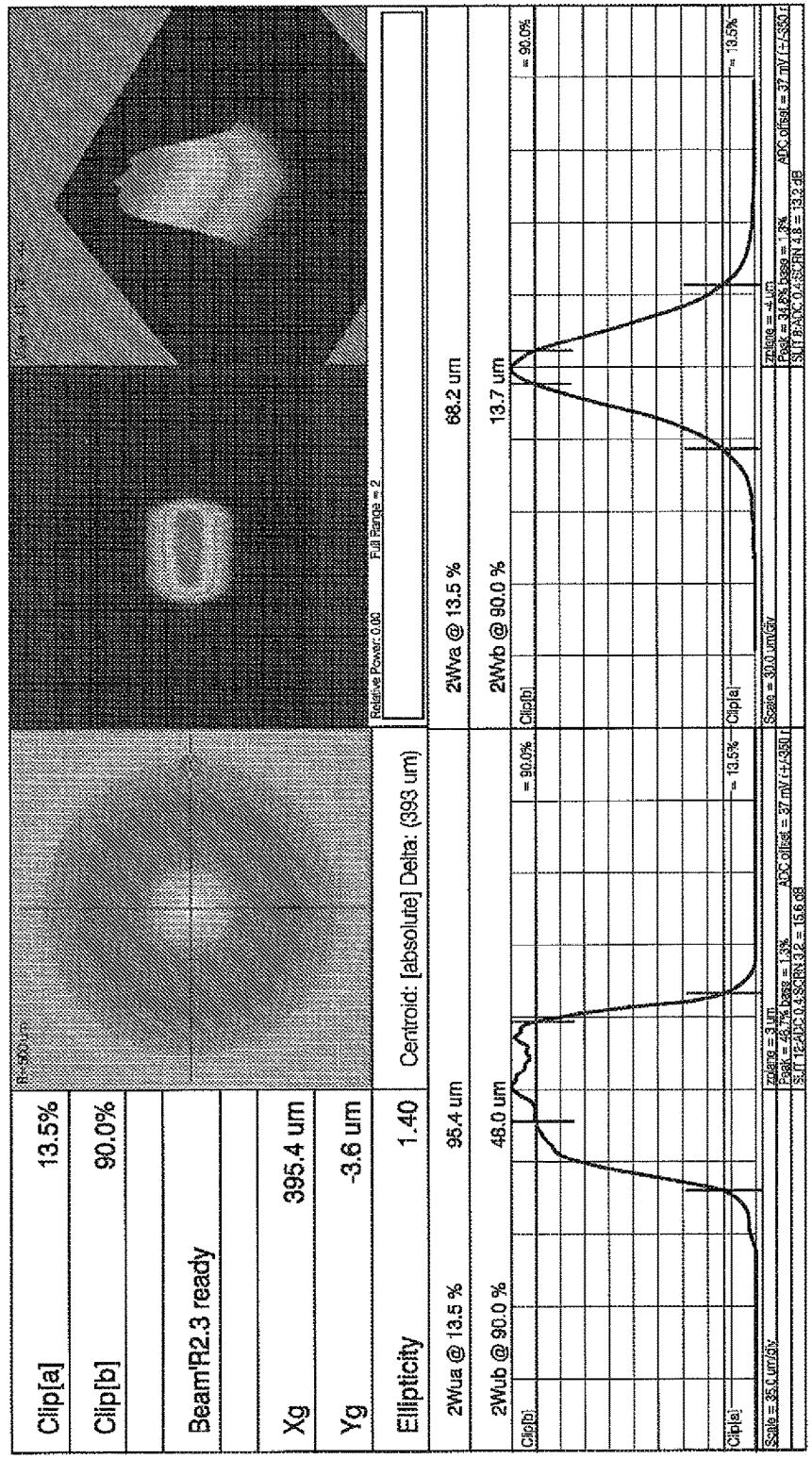
FIG. 9C depicts a blue laser system, with a glass window at 45 degrees, at flat top focus with associated profiles.

FIG. 9C, entitled "Blue Laser Beam with a 3 mm 45 Degree Window—At Flat Top Focus", presents data from a blue laser beam focused at a camera with a glass window titled at about 45 degrees incident to the laser beam. The glass window is about 3 millimeters thick and constructed from glass. The focusing was determined by where the maximum flat top profile intensity and width occurred. The reverse is occurring in this figure as the last. In this case, the flat top beam with is at about 90% intensity for about 48 micrometers. However, the Gaussian has gone well over about 2 micrometers at about 90% beam intensity (to about 13.7 micrometers). The difference between this data and the data from the first figure is due to introduction of aberrations from passing the laser beam through the optical element. Noise in the acquired data will also increase with this beam profile.

Figure 9D:
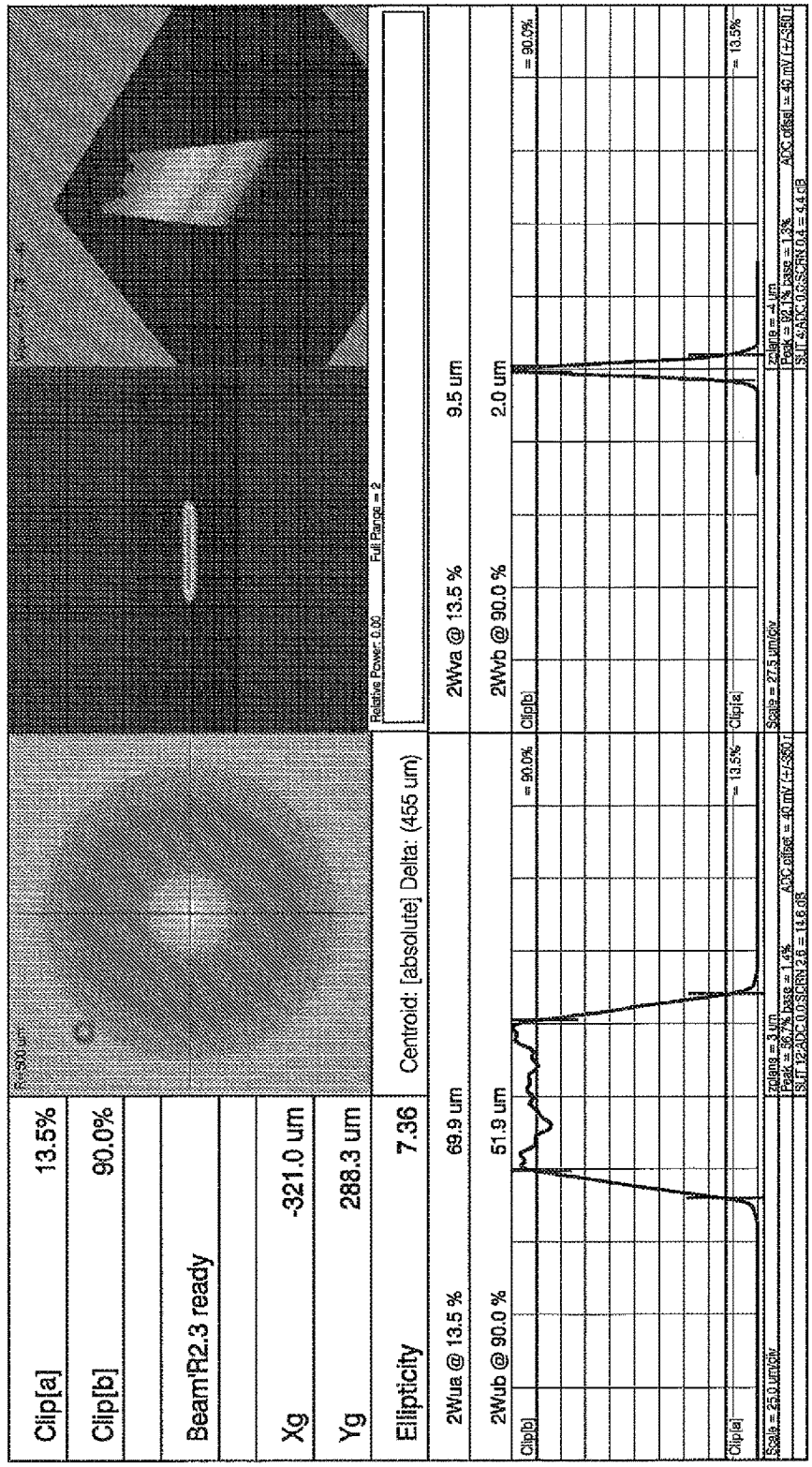
FIG. 9D depicts a blue laser system, with two dichroic cubes, at focus with associated profiles.

FIG. 9D, entitled "Blue Laser Beam at Focus with 2 Dichroic Cubes", presents data from a blue laser being focused through two optical elements (dichroic cubes) and onto a camera. When compared to the first figure in this example, the laser beam profile matches very closely which shows that very little, if any, aberrations have been introduced by the two dichroic cubes. This is because the flat top laser beam profile is maintained when propagated through two dichroic cubes. The flat top focus has a beam width of about 51.9 micrometers and the Gaussian focus has a width of about 2 micrometers. Such a beam profile will produce high quality data unlike the beam profile coming out of the about 3 millimeter glass windows which will likely produce unusable data in flow cytometry and other applications.

Example 7

Percent Coefficient of Variation

In flow cytometry the degree to which replicate measurements of a particle agree with one another can be characterized by the coefficient of variation (CV). A measure of the variability in signal intensity is generated as particles pass repeatedly though a light source (e.g. a laser beam). The variability is expressed as a percentage of the average signal intensity. This statistical measurement is well known in the art and is defined as 100 times the standard deviation divided by the mean. Generally, a lower CV means that replicate measurements agree with one another. Each of the following figures present two graphical plots. The dotted plots display CV and the dashed plots display intensity. The y-axis is normalized to percentage where 1.0 is 100 percent. The x-axis has units in micrometers. The laser beam is converging in each of these data sets. The data following data was collected using a Data Ray Beam'R2. Laser focus was optimized by focusing the beam height to about 10 micrometers. The coefficients of variation (CVs) were calculated using about a 50 micrometer window width. The plots shown in FIGS. 10A-10C display normalized intensity as well as a moving window CV.

Figure 10A:
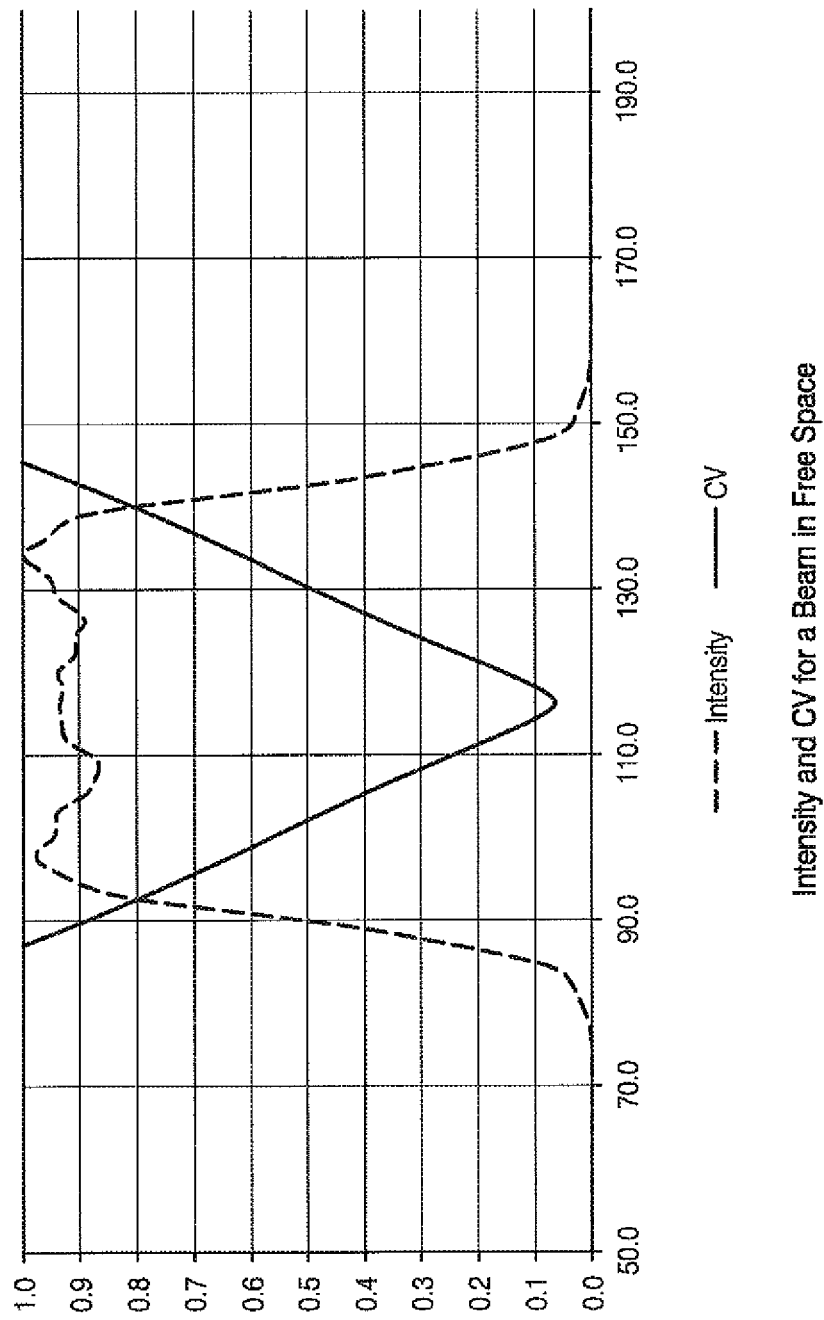
FIG. 10A is a plot of intensity and coefficient of variation data for a laser beam focused with no dichroic optical elements in the optical path.

The data in FIG. 10A, entitled "Intensity and CV for a Beam in Free Space", was acquired by focusing a laser beam onto a camera with no dichroic optical elements in the optical path. The data shows a flat top laser beam profile where about 50 micrometers of the laser beam is above about the 90% intensity level. The CV drops to about 0.5 or about 5%.

Figure 10B:
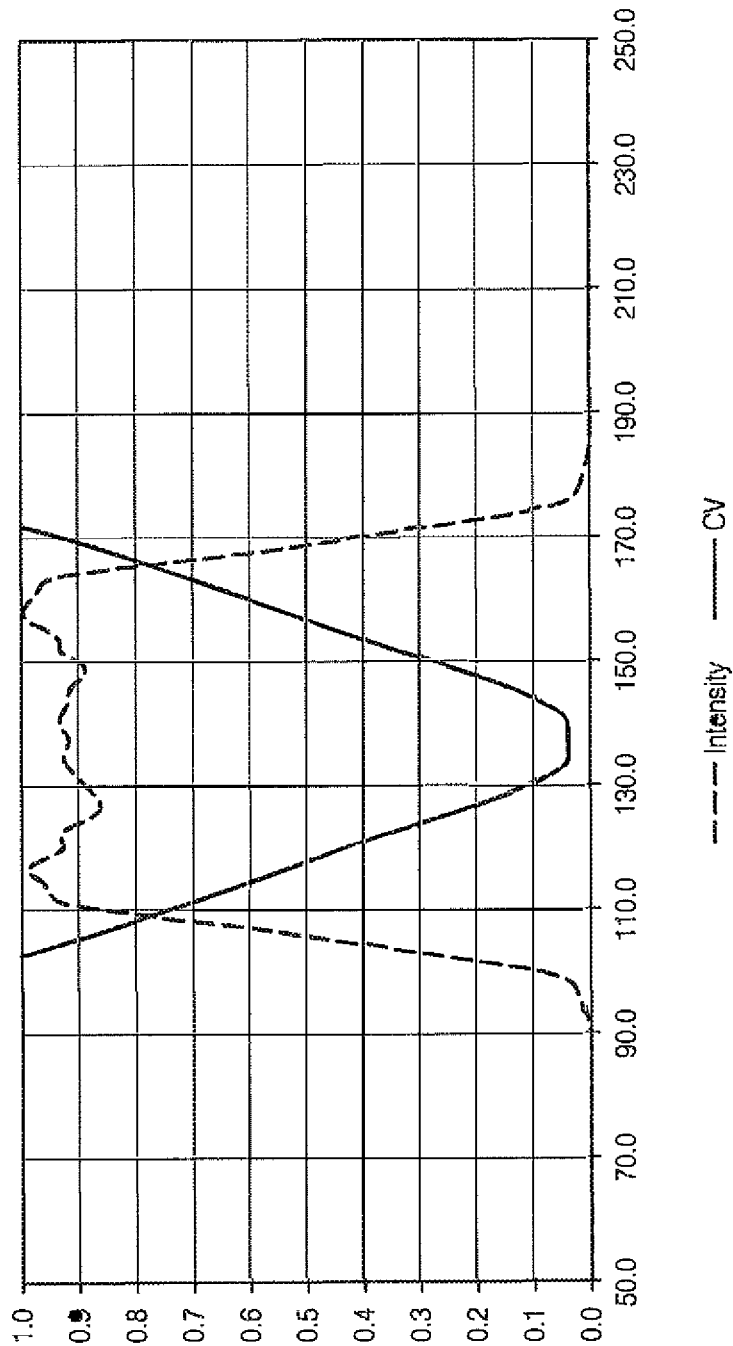
FIG. 10B is a plot of intensity and coefficient of variation data for a laser beam propagated through a dichroic cube.

The data in FIG. 10B, entitled "Intensity and CV for a Beam Propagated Through about a 15 mm BK7 Dichroic Cube", was acquired by focusing a laser beam onto a camera where the laser beam was propagated through about a 15 millimeter BK 7 dichroic cube. BK7 glass is known for its high rate of transmission and for having an index of refraction of about 1.5 depending on the wavelength of light being transmitted. The data shows a flat top laser beam profile where about 50 micrometers of the laser beam is above about the 90% intensity level. The CV drops to about 0.5 or 5%. More specifically, the laser beam profile is unchanged with little or no aberrations being introduced.

Figure 10C:
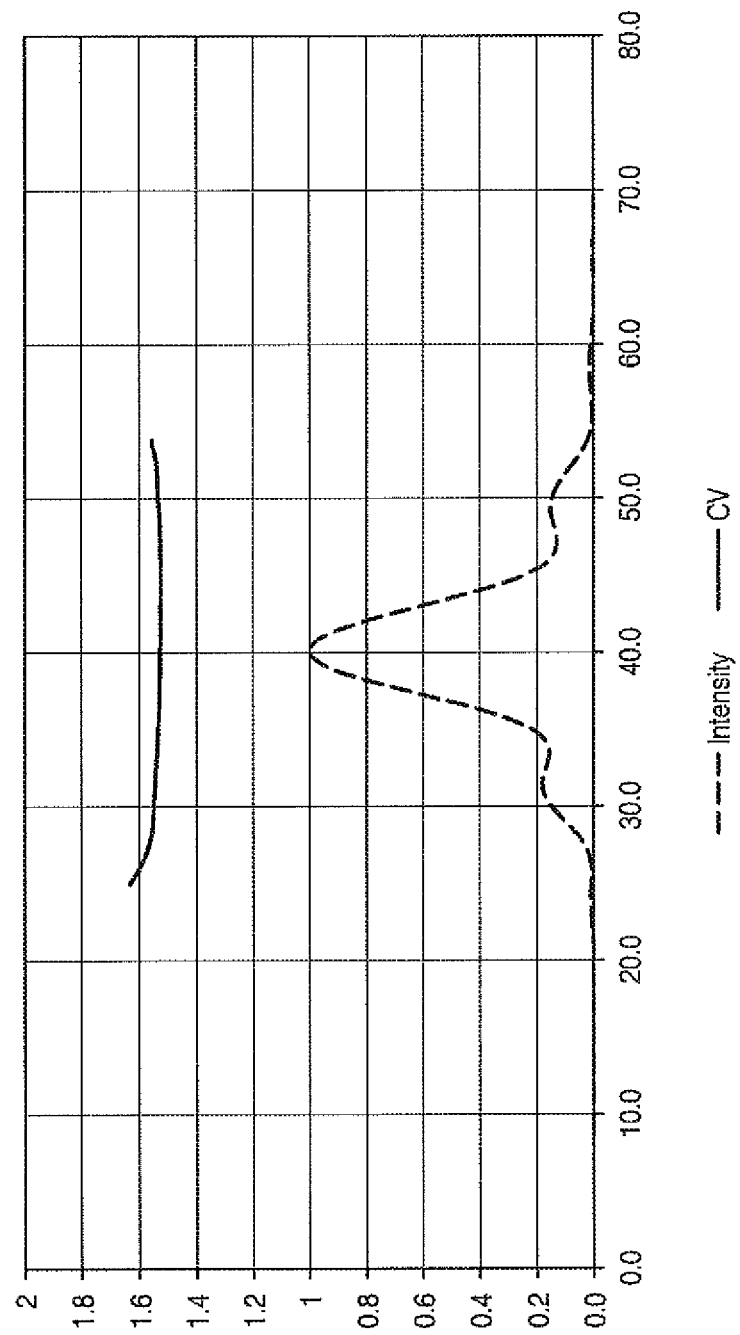
FIG. 10C is a plot of intensity and coefficient of variation data for a laser beam propagated through a dichroic plate at a 45 degree incident angle.

The data in FIG. 10C, entitled "Intensity and CV for a Beam Propagated Through about a 3 mm BK7 Plate at about a 45 Degree Incident Angle", was acquired by focusing a laser beam onto a camera where the laser beam was propagated through about a 3 millimeter BK 7 dichroic plate at about a 45 degree angle of incidence. The data shows a laser beam profile where about significantly less than about 50 micrometers of the laser beam is above about the 90% intensity level. The CV is of such poor quality that the y-axis has been altered to accommodate the high CV. A laser beam profile such as this has had multiple severe aberrations introduced. Data collected would contain large amounts of noise and could be unusable.

In this example, it is clearly shown that the standard flat plate dichroic plates are unable to accommodate the converging laser beam in this system. A preferable CV is about 10% or less. A more preferable CV is about 9% or less. An even more preferable CV is about 8% or less. An even more preferable CV than 8% is about 7% or less. An even more preferable CV than 7% is about 6% or less. An even more preferable CV than 6% is about 5% or less. An even more preferable CV than 5% is about 4% or less. An even more preferable CV than 4% is about 3% or less. An even more preferable CV than 3% is about 2% or less. A most preferable CV is about 1% or less.

The current optical system can achieve such CV values from each individual light source (e.g. laser beam) by being able to independently focus the light source into a converging light beam at the beginning of the optical train and then pass that converging light beam through dichroic cubes instead of the dichroic plate (ubiquitous optical element in the art) that is often angled at about 45 degrees incident to the incoming light source.

An optimal light beam profile has a flat top. An optimal light beam width is between about 30 to about 70 micrometers. A more optimal light beam width is between about 35 to about 65 micrometers. A more optimal light beam width is between about 40 to about 60 micrometers. A more optimal light beam width is between about 45 to about 55 micrometers.

An optical train can comprise one or more dichroic cubes, one or more dichroic plates, one or more mirrors, one or more lenses, one or more spinning disks, one or more filter wheels, one or more objectives, elements capable of reflection or transmission, or any known optical element in the art. Additionally, optical elements can comprise plastic, glass, or any other known or useful material or combination of materials. For example, a glass surface can be coated with a reflective material where the reflective material can be a material other than glass.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed:

1. A system, comprising:
   a flow cell configured to receive a fluid sample, the flow cell having an interrogation zone;
   a first optical subunit comprising: (i) a first light source configured to produce a first light beam, and (ii) a first converging element configured to convert the first light beam into a first converging light beam;
   a second optical subunit comprising: (i) a second light source configured to produce a second light beam, and (ii) a second converging element configured to convert the second light beam into a second converging light beam; and
   an optical train comprising a dichroic element configured to direct the first and second converging light beams to the interrogation zone, wherein the first and second converging light beams are communicated directly from the dichroic element to the interrogation zone.

2. The system of claim 1, wherein the dichroic element is configured to receive the first converging light beam through an entry face, and wherein the entry face is configured to be at least near perpendicular to the first converging light beam.

3. The system of claim 2, wherein the dichroic element is configured to transmit the first converging light beam as a first transmitted converging light beam through an exit face, and wherein the exit face is configured to be at least near perpendicular to the first transmitted converging light beam.

4. The system of claim 3, wherein the dichroic element is additionally configured to receive the second converging light beam through a second entry face, and wherein the second entry face is configured to be at least near perpendicular to the second converging light beam.

5. The system of claim 4, wherein the dichroic element is configured to transmit the second converging light beam as a second transmitted converging light beam through the exit face.

6. The system of claim 2, wherein the entry face is configured to allow all parts of the first converging light beam to simultaneously enter the dichroic element.

7. The system of claim 1, wherein the dichroic element comprises prisms.

8. The system of claim 7, wherein the dichroic element comprises two prisms arranged to form a cube.

9. The system of claim 8, wherein the dichroic element includes a wavelength selective coating located between the two prisms.

10. The system of claim 1, wherein the optical train is configured to maintain a flat top profile or a Gaussian profile of the first and second converging light beams as the first and second converging light beams are directed to the interrogation zone.

11. The system of claim 1, wherein the optical train is configured to introduce little or no aberrations into the first and second converging light beams as the first and second converging light beams are directed to the interrogation zone.

12. The system of claim 11, wherein the aberrations are spherical aberrations, astigmatisms, linear comas and cubic comas.

13. The system of claim 1, wherein the system further comprises:
   a third optical subunit comprising: (i) a third light source configured to produce a third light beam, and (ii) a third converging element configured to convert the third light beam into a third converging light beam; and
   wherein the optical train is configured to direct the third converging light beam to the interrogation zone.

14. The system of claim 1, wherein the optical train is configured to direct the first and second converging light beams to the interrogation zone with spatial separation upon entry of the interrogation zone.

15. The system of claim 14, wherein the first and second optical subunits are each affixed to an opto-mechanical mount, wherein each opto-mechanical mount is operable to adjust the spatial separation of the first and second converging light beams.

16. The system of claim 1, wherein the first and second converging elements are convex lenses.

17. The system of claim 1, wherein the optical train does not include a plate dichroic element.

18. The system of claim 1, wherein the first light beam and the second light beam are not collimated.

19. The system of claim 1, wherein the flow cell is configured to receive a flow with a plurality of particles through the interrogation zone.

* * * * *